(12) United States Patent
Mor et al.

(10) Patent No.: US 7,666,583 B2
(45) Date of Patent: Feb. 23, 2010

(54) IDENTIFICATION OF CANCER PROTEIN BIOMARKERS USING PROTEOMIC TECHNIQUES

(75) Inventors: Gil G. Mor, Cheshire, CT (US); David C. Ward, Las Vegas, NV (US); Patricia Bray-Ward, Las Vegas, NV (US)

(73) Assignee: Yale University, New Haven, CT (US)

( * ) Notice: Subject to any disclaimer, the term of this patent is extended or adjusted under 35 U.S.C. 154(b) by 154 days.

(21) Appl. No.: 11/037,889

(22) Filed: Jan. 18, 2005

(65) Prior Publication Data

US 2005/0214826 A1    Sep. 29, 2005

Related U.S. Application Data

(60) Provisional application No. 60/545,581, filed on Feb. 19, 2004, provisional application No. 60/545,900, filed on Feb. 20, 2004.

(51) Int. Cl.
*C12Q 1/00*     (2006.01)
*C40B 30/00*    (2006.01)
(52) U.S. Cl. .............................. 435/4; 506/7
(58) Field of Classification Search .................. 506/7; 435/4
See application file for complete search history.

(56) References Cited

U.S. PATENT DOCUMENTS

| | | | |
|---|---|---|---|
| 5,583,110 A | 12/1996 | Altchek et al. | |
| 6,071,914 A | 6/2000 | Cincotta et al. | |
| 6,235,474 B1 | 5/2001 | Feinberg | |
| 6,642,009 B2 | 11/2003 | Hung | |
| 2003/0044862 A1 | 3/2003 | Giaccia et al. | |
| 2003/0180747 A1 | 9/2003 | Hruban et al. | |
| 2003/0198970 A1 | 10/2003 | Roberts | |
| 2003/0219812 A1 | 11/2003 | Quay et al. | |
| 2003/0232398 A1 | 12/2003 | MacMurray et al. | |
| 2004/0023288 A1 | 2/2004 | Ridder et al. | |
| 2004/0072189 A1 | 4/2004 | Smith et al. | |
| 2005/0069963 A1 | 3/2005 | Lokshin et al. | |

FOREIGN PATENT DOCUMENTS

| | | |
|---|---|---|
| EP | 1 256 354 | 11/2002 |
| JP | 02083337 | 3/1990 |
| WO | WO 94/19004 A1 | 9/1994 |
| WO | WO 00/55629 | 9/2000 |
| WO | WO01/40271 | 6/2001 |
| WO | WO01/53837 | 7/2001 |
| WO | WO 01/54713 | 8/2001 |
| WO | WO 01/70985 A2 | 9/2001 |
| WO | WO03/005197 | 6/2003 |
| WO | WO 03/051917 A2 | 6/2003 |
| WO | WO03/102148 | 12/2003 |

OTHER PUBLICATIONS

Sancak et al., Internal Medicine Journal, 2004, 34: 310-315.*
Jacobs et al., Molecular & Cellular Proteomics, 2004, 3.4: 355-366.*
Taylor et al., 2001, Cancer Screening in a High Risk Population: a Clinical Trial, Ultrasound in Med. & Biol., 27(4): 461-466.*
Mor et al., 2005, Serum Protien Markers for Early Detection of Ovarian Cancer, PNAS, 102(21): 7677-7682.*
Zhang et al., Cancer Research, 2004, 64: 5882-5890.*
Baron-Hay et al., Clinical Cancer Research, 2004, 10: 1796-1806.*
Jha et al., Int. J. Gynecol. Obstet., 1991, 36: 33-38.*
Tessitore et al., Int. J. Mol. Med., 2000, 5: 421-426.*
Zhang et al., Mol. Cell. Biol., 2003, 23(18): 6507-6519.*
Sawiris et al., 2002, Development of a Highly Specialized cDNA Array for the Study and Diagnosis of Epithelial Ovarian Cancer, Cancer Research, 62: 2923-2928. 20 additional pages for the gene listing.*
Choi et al., 2005 (epub Nov. 2, 2004), Expression of Leptin Receptors and Potential Effects of Leptin on the Cell Growth and Activation of Mitogen-activated Protein Kinases in Ovarain Cancer Cells, 90(1): 207-210.*
Schorge et al., 2004, Osteopontin as an Adjunct to CA125 in Detecting Recurrent Ovarain Cancer, Clinical Cancer Research, 10: 3474-3478.*
Yoshida et al., 1998, Ovarian dysgerminoma showing high serum levels and positive immunostaining of placental alkaline phosphate and neuron-specific enolase associated with elevation of serum prolactin level, European Journal of Obsterics & Gynecology, 81: 123-128.*
Baron-Hay et al., 2004, "Elevated serum-insulin-like growth factor binding protein-2 as a prognostic marker in patients with ovarian cancer," Clin. Cancer Res. 10(5):1796-1806.
Bowen et al., 2000, "Downregulation of long-form prolactin receptor mRNA during prolactin-induced regression," Eur. J. Endocrinol. 143(2):285-292.
Brakora et al., 2004, "Utility of osteopontin as a biomarker in recurrent epithelial ovarian cancer," Gynecol. Oncol. 93(2):361-365.
Crump et al., 2000, "Ovarian cancer tumor marker behavior in asymptomatic healthy women: implications for screening," Cancer Epidemiol. Biomarkers Prev 9(10):1107-1111.

(Continued)

*Primary Examiner*—Amber D. Steele
(74) *Attorney, Agent, or Firm*—Wolf, Greenfield & Sacks, P.C.

(57) ABSTRACT

The claimed invention describes methods to diagnose or aid in the diagnosis of cancer. The claimed methods are based on the identification of biomarkers which are particularly well suited to discriminate between cancer subjects and healthy subjects. These biomarkers were identified using a unique and novel screening method described herein. The biomarkers identified herein can also be used in the prognosis and monitoring of cancer. The invention comprises the use of leptin, prolactin, OPN and IGF-II for diagnosing, prognosis and monitoring of ovarian cancer.

32 Claims, 6 Drawing Sheets

OTHER PUBLICATIONS

DeSouza et al., 2004, "Fastin ghrelin levels in physically active women: relationship with menstrual disturbances and metabolic hormones," J. Clin. Endocrinol. Metab. 89(7):3536-3542.

Dixit et al., 2004, "Ghrelin inhibits leptin- and activation-induced proinflammatory cytokine expression by human monocytes and T cells," J. Clin. Invest. 114(1):57-66.

Furger et al., 2001, "The functional and clinical roles of osteopontin in cancer and metastasis," Curr. Mol. Med. 1(5):621-632.

Gutzman et al., 2004, "Multiple kinase cascades mediate prolactin signals to activating protein-1 in breast cancer cells," Mol. Endocrinol. 18(12):3064-3075.

Ho, 2003, "Estrogen, Progesterone and Epithelial Ovarian Cancer," Reprod. Biol and Endocrin 1:73.

Ishikawa et al., 2004, "Enhanced expression of leptin and leptin receptor (OB-R) in human breast cancer," Clin. Cancer Res. 10(13):4325-4331.

Jacobs and Menon, 2004, "Progress and challenges in screening for early detection of ovarian cancer," Mol. Cell Proteomics 3(4):355-366.

Jha et al., 1991, "Use of serum prolactin for monitoring the therapeutic response in ovarian malignancy," Int. J. Gynaecol. Obstet. 36(1):33-38.

Kitawaki et al., 1999, "Leptin directly stimulates aromatase activity in human lutenized granulosa cells," Mol. Human Reprod. 5(8):708-713.

Koopmann et al., 2004, "Evaluation of osteopontin as biomarker for pancreatic adenocarcinoma," Cancer Epidemiol. Biomarkers Prev. 13(3):487-491.

Lu et al., 2004, Selection of potential markers for epithelial ovarian cancer with gene expression arrays and recursive descent partition analysis, Clin Cancer Res. 10(10):3291-3300.

Malaguarnera et al., "Prolactin increases HO-1 expression and induces VEGF production in human macrophages," J. Cell. Biochem. 93(1):197-206.

McIntosh et al., 2004, "Combining CA 125 and SMR serum markers for diagnosis and early detection of ovarian carcinoma," Gynecol. Oncol. 95(1):9-15.

Menon, 2004, "Ovarian cancer screening," Cmaj 171(4):323-324.

Motta el al., 2004, "Leptin and prolactin modulate the expression of SOCS-1 in association with interleuki-6 and tumor necrosis factor-alpha in mammary cells: a role in differential secretory epithelium," Regul Pept. 121(1-3):163-170.

Mujagic and Mujagic, 2004, "Importance of serum prolactin determination in metastatic breast cancer patients," Croat. Med. J. 45(2)176-180.

O'Regan et al., 2002, "Osteopontin as a biomarker for ovarian cancer," JAMA 287(24):3208-3210.

Oberbeck, 2004, "Therapeutic implications of immune-endocrine interactions in the critically ill patients," Curr. Drug. Targets Immune Endocr. Metabol. Disord. 4(2):129-139.

Perks et al., 2004, "Prolactin acts as a potent survival factor for human breast cancer cell lines," Br. J. Cancer. 91(2):305-311.

Perumal et al., 1998, "Prolactin as a tumour marker in cancer of the cervix," J. Obstet. Gynaecol. 18(3):260-262.

Petricoin et al., 2002, "Use of proteomic patters in serum to identify ovarian cancer," Lancet 359(9306):572-577.

Plebani et al., 1996, "Serum tumor markers in colorectal cancer staging, grading, and follow-up," J. Surg. Oncol. 62(4):239-244.

Rittling and Chambers, 2004, "Role of osteopontin in tumour progression," Br. J. Cancer 90(10):1877-1881.

Rose et al., 2004, "Obesity, adipocytokines, and insulin resistance in breast cancer," Obesity Reviews 5(3):153.

Sancak et al., 2004, "No association between serum levels of insulin-like growth factor-I, vascular endothelial growth factor, prolactin and clinicopathological characteristics of breast carcinoma after surgery," Intern. Med. J. 34(6):310-315.

Santin et al., 2004, "Gene expression profiles in primary ovarian serous papillar tumors and normal ovarian epithelium: identification of candidate molecular markers for ovarian cancer diagnosis and therapy," Int. J. Cancer 112(1):14-25.

Schorge et al., 2004, "Osteopontin as an adjunct to CA125 in detecting recurrent ovarian cancer," Clin. Cancer Res. 10(1):3474-3478.

Schweitzer et al., 2002, "Multiplexed protein profiling on microarrays by rolling-circle amplification," Nat. Biotechnol. 20(4):359-365.

Singer et al., 2004, "Insulin-like growth factor (IGF)-I and IGF-II serum concentrations in patients with benign and malignant breast lesions: free IGF-II is correlated with breast cancer size," Clin. Cancer Res. 15(10):4003-4009.

Skates et al., 2004, "Preoperative sensitivity and specificity for early-stage ovarian cancer when combining cancer antigen CA-125II, CA 15-3, CA 72-4, and macrophage colony-stimulating factor using mixtures of multivariate normal distributions," J. Clin. Oncol. 22(20):4059-4066.

Tessitore et al., 2000, "Leptin expression in colorectal and breast cancer patients," Int. J. Mol. Med. 5(4):421-426.

Tworoger et al., 2004, "Plasma prolactin concentrations and risk of postmenopausal breast cancer," Cancer Res. 64(18):6814-6819.

Unni et al., 2004, "Osteopontin is a potential target gene in mouse mammary cancer chemoprevention by Se-methylselenocysteine," Breast Cancer Res. 6(5):R586-592.

Urban et al., 2003, "Ovarian cancer screening," Hematol. Oncol. Clin. North Am. 17(4):989-1005.

Wai and Kuo, 2004, "The role of osteopontin in tumor metastasis," J. Surg. Res. 121(2):228-241.

Weber, 2001, "The metastasis gene osteopontin: a candidate target for cancer therapy," Biochim. Biophys. Acta 1552(2):61-85.

Woolas et al., 1993, "Elevation of multiple serum markers in patients with stage I ovarian cancer," J. Natl. Cancer Inst. 85(21):1748-1751.

Zhang et al., 2003, "Growth factor signaling induces metastasis genes in transformed cells: molecular connection between Akt kinase and osteopontin in breast cancer," Mol. Cell. Biol. 23(18):6507-6519.

Zhang et al., 2004, "Three biomarkers identified from serum proteomic analysis for the detection of early stage ovarian cancer," Cancer Res. 64(16):5882-5890.

Gorelik et al., 2005, Multiplexed Immunobead-Based Cytokine Profiling for Early Detection of Ovarian Cancer, Cancer Epidemiology, Biomarkers & Prevention 14(4):981-987.

Yao et al., 2003, Differential Gene Expression in Chemically Induced Mouse Lung Adenomas, Neoplasia 5(1):41-52.

Visintin, I. et al., Diagnostic markers for early detection of ovarian cancer. Clin Cancer Res. Feb. 15, 2008;14(4):1065-72. Epub Feb. 7, 2008.

Gaja et al., [The importance of leptin in oncology—hypothesis or facts?] Vnitr Lek. Apr. 2001;47(4): Review. Czech. Medline Abstract. Accession No. 15635891, abstract only.

\* cited by examiner

Screening Method used for the Detection of EOC Protein Biomarkers in serum

| Screening Phase | Screening Process | Results |
|---|---|---|
| I | 169 Proteins assayed by RCA microarrays using serum from 46 subjects (28 Healthy and 18 newly diagnosed Cancer patients). | 35 differentially expressed proteins identified with $p<0.05$. |
| II | RCA microarray analysis comparing serum from the same 28 healthy subjects with 40 new patients @ recurrent EOC. | 10 of 35 proteins identified in phase I retained as potential markers for future testing ($p<0.001$). |
| III | 6 of the most statistically significant proteins selected for ELISA assays using samples from 50 subjects (25 healthy and 25 Cancer) from phase I and II study. | A combination of 4 proteins provided 100% accuracy in classification of control and cancer patients in test group. |
| IV | New healthy subjects (106) and 100 new patients with EOC (24 stage I/II; 76 stage III/IV) were assayed blind using ELISA assays for the four biomarkers. | Statistical analysis of data after sample decoding show a 96% specifically and 97% sensitivity in classifying samples. A simple binary analyte split-point assay developed. |
| V | 40 new unknown samples assayed by 4-analyte ELISA and classified using binary split-point assay as normal (score 0/1) or cancer (score 2-4). | 38 of 40 samples correctly classified; (1FP and 1FN). |

Fig. 1

IDENTIFICATION OF CANCER PROTEIN BIOMARKERS USING PROTEOMIC TECHNIQUES

CROSS-REFERENCE TO RELATED APPLCATIONS

The teachings of both U.S. Provisional Application No. 60/545,581, filed Feb. 19, 2004, and U.S. Provisional Application No. 60/545,900, filed Feb. 20, 2004 are incorporated by reference herein.

FUNDING

This invention was made with government support under grant number DE-FG02-ER63462 awarded by the United States Department of Energy. The government has certain rights in the invention.

BACKGROUND OF THE INVENTION

Epithelial Ovarian Cancer (EOC) is the fourth leading cause of cancer-related death in women in the United States and the leading cause of gynecologic cancer death. EOC is characterized by few early symptoms, presentation at an advanced stage, and poor survival. This year approximately 25,000 women will be newly diagnosed with ovarian cancer and 13,500 will die from the disease. The major limitations in the treatment of ovarian cancer are: i) the lack of an early detection tumor marker, ii) the resistance to chemotherapeutic agents, and iii) the lack of obvious early warning symptoms. The high mortality rate is related to the inability to detect early disease, as approximately 70% of patients are diagnosed at an advanced stage. In patients diagnosed with early (stage I or II) disease, the five-year survival rate ranges from 60 to 90% depending on the degree of tumor differentiation. Although the clinical presentation of heritable cancer is similar to the high-risk population, the onset of ovarian cancer in this group tends to occur 10-15 years earlier than that of the general population (early 40's rather than 60's). One of the most promising approaches to management of EOC is early detection. The most commonly used test, CA125 identifies a group of cell surface glycoproteins that have uncertain biological behavior and very limited clinical application for the detection of early stage disease. As a single marker, CA125 has a predictive value of less than 10% in Stage I. Even the addition of ultrasound screening to CA125 measurement improves the positive prediction value to only about 20%. The lack of specific markers for ovarian cancer makes it difficult to achieve the clinical objective of screening and early detection.

Presently there is no commercially available test that can be used to diagnose either early or advanced stage ovarian cancer. Thus, the identification of a test that can be used to diagnose early or advance stage ovarian cancer is required.

BRIEF SUMMARY OF THE INVENTION

The invention comprises a method for diagnosing or aiding in the diagnosis of cancer in a subject comprising comparing the expression of one or more biomarkers in a sample from a subject to a predetermined standard for each said one or more biomarkers; wherein said one or more biomarkers are selected from the group consisting of: 6Ckine, ACE, BDNF, CA125, E-Selectin, EGF, Eot2, ErbB1, follistatin, HCC4, HVEM, IGF-II, IGFBP-1, IL-17, IL-1srII, IL-2sRa, leptin, M-CSF R, MIF, MIP-1a, MIP3b, MMP-8, MMP7, MPIF-1, OPN, PARC, PDGF Rb, prolactin, ProteinC, TGF-b RIII, TNF-R1, TNF-a, VAP-1, VEGF R2 and VEGF R3; and wherein a significant difference in the expression of said one or more biomarkers in said sample as compared to a predetermined standard of each said one or more biomarkers diagnoses or aids in the diagnosis of cancer.

In one embodiment, the predetermined standard corresponds to: (a) the expression level of said biomarker in healthy subjects, or (b) the expression level of said biomarker in non-cancerous tissue from the same subject.

In one embodiment, the method further comprises comparing the expression of two or more biomarkers, wherein the diagnosis of cancer is based on a score-based classification method. In one embodiment, the method comprises comparing the expression of m different biomarkers; wherein each biomarker is assigned a score of 0 or 1, wherein a biomarker is assigned a score of 0 if the expression of said biomarker is not significantly different from the expression of said biomarker in a predetermined standard and wherein a biomarker is assigned a score of 1 if the expression of said biomarker is significantly different from the expression of said biomarker in a predetermined standard; wherein the subject is assigned an overall score which corresponds to the sum of the assigned scores from m different markers; and wherein a given threshold (t) is used to diagnose or aid in the diagnosis of cancer.

In another embodiment, the method comprises comparing the expression of two or more biomarkers, wherein the diagnosis of cancer is made by comparing the expression profile of said two or more biomarkers to a predetermined standard profile for said biomarkers, and wherein a difference in the profiles diagnoses or aids in the diagnosis of cancer. In one embodiment, the predetermined standard profile is determined by comparing the expression of said two or more biomarkers in cancer subjects to the expression of said two or more biomarkers in healthy subjects using a machine learning technique. In one embodiment, the predetermined standard profile is determined by comparing the expression of said two or more biomarkers in cancer subjects and in healthy subjects using support vector machines, K-nearest neighbor classifier, or classification tree analysis.

In one embodiment, the method is for the diagnosis for ovarian cancer, and the method further comprises detecting an additional biomarker for ovarian cancer which is not identified in Table 2. In one embodiment, the additional biomarker for ovarian cancer may be selected from the group consisting of: human stratum corneum chymotryptic enzyme (HSCCE), kallikrein 4, kallikrein 5, kallikrein 6 (protease M), kallikrein 8, kallikrein 9, kallikrein 10, CA125, CA15-3, CA19-9, OVX1, lysophosphatidic acid (LPA), carcinoebryonic antigen (CEA), macrophage colony-stimulating factor (M-CSF), prostasin, CA54-61, CA72, HMFG2, IL-6, IL-10, LSA, M-CSF, NB70K, PLAP, TAG72, TNF, TPA, UGTF, WAP four-disulfide core domain 2 (HE4), matrix metalloprotease 2, tetranectin, inhibin, mesothelyn, MUC1, VEGF, CLDN3, NOTCH3, E2F transcription factor 3 (E2F3), GTPase activating protein (RACGAP1), hemotological and neurological expressed 1 (HN1), apolipoprotein A1, laminin, claudin 3, claudin 4, tumor-associated calcium signal transducer 1 (TROP-1/Ep-CAM), tumor-associated calcium signal transducer 2 (TROP-2), ladinin 1, S100A2, SERPIN2 (PAI-2), CD24, lipocalin 2, matriptase (TADG-15), stratifin, transforming growth factor-beta receptor III, platelet-derived growth factor receptor alpha, SEMACAP3, ras homology gene family member I (ARHI), thrombospondin 2, disabled-2/differentially expressed in ovarian carcinoma 2 (Dab2/DOC2), and haptoglobin-alpha subunit. In another embodiment, the additional biomarker for ovarian cancer is the truncated form of transthyretin or the cleavage fragment of inter-alpha-trypsin inhibitor heavy chain H4 identified by Zhang et al., *Cancer Res.* 64(16):5882-90 (2004). In one embodiment, the additional biomarker for ovarian cancer is CA125.

The above described methods of diagnosing or aiding in the diagnosis of cancer can be applied to diagnose or aid in the diagnosis of any cancer or tumor. In one embodiment, the method is for the diagnosis of breast cancer. In one embodiment, the method is for the diagnosis of colon cancer. In another embodiment, the method is for the diagnosis of cervical cancer.

The invention also comprises a method for diagnosing or aiding in the diagnosis of cancer in a subject comprising comparing the expression of one or more biomarkers in a sample from a subject to a predetermined standard for each said one or more biomarkers; wherein said one or more biomarkers are selected from the group consisting of: prolactin, MIF, OPN, IGF-II, E-Selectin, leptin, EGF, IL-17, MPIF-1, and IL-2sRa; and wherein a significant difference in the expression of said one or more biomarkers in said sample as compared to a predetermined standard of each said one or more biomarkers diagnoses or aids in the diagnosis of cancer.

The invention also comprises a method for diagnosing or aiding in the diagnosis of cancer in a subject comprising comparing the expression of one or more biomarkers in a sample from a subject to a predetermined standard for each said one or more biomarkers; wherein said one or more biomarkers are selected from the group consisting of: leptin, prolactin, OPN and IGF-II; and wherein a significant difference in the expression of one or more biomarkers in said sample as compared to a predetermined standard of each said one or more biomarkers diagnoses or aids in the diagnosis of cancer.

The invention also comprises a method for diagnosing or aiding in the diagnosis of cancer in a subject comprising comparing the expression of the following four biomarkers: leptin, prolactin, OPN and IGF-II, in a sample from a subject to a predetermined standard for each said biomarkers; wherein a significant difference in the expression of two or more of said biomarkers in said sample as compared to a predetermined standard of each said one or more biomarkers diagnoses or aids in the diagnosis of cancer.

The invention also comprises a method for diagnosing or aiding in the diagnosis of ovarian cancer in a subject comprising comparing the expression of the following four biomarkers: leptin, prolactin, OPN and IGF-II, in a sample from a subject to a predetermined standard for each said biomarkers; wherein a significant difference in the expression of two or more of said biomarkers in said sample as compared to a predetermined standard of each said one or more biomarkers diagnoses or aids in the diagnosis of cancer.

The invention also comprises a method for diagnosing or aiding in the diagnosis of breast cancer in a subject comprising comparing the expression of the following four biomarkers: leptin, prolactin, OPN and IGF-II, in a sample from a subject to a predetermined standard for each said biomarkers; wherein a significant difference in the expression of two or more of said biomarkers in said sample as compared to a predetermined standard of each said one or more biomarkers diagnoses or aids in the diagnosis of cancer.

The invention also comprises a method for diagnosing or aiding in the diagnosis of colon cancer in a subject comprising comparing the expression of the following four biomarkers: leptin, prolactin, OPN and IGF-II, in a sample from a subject to a predetermined standard for each said biomarkers; wherein a significant difference in the expression of two or more of said biomarkers in said sample as compared to a predetermined standard of each said one or more biomarkers diagnoses or aids in the diagnosis of cancer.

In one embodiment, the above described methods comprise comparing the expression of prolactin and/or OPN to a predetermined standard of said biomarker, wherein an increase in the expression of said biomarker as compared to the predetermined standard for said biomarker diagnoses or aids in the diagnosis of cancer.

In one embodiment, the above described methods comprise comparing the expression of leptin and/or IGF-II to a predetermined standard of said biomarker, and wherein a decrease in the expression of said biomarker as compared to the predetermined standard for said biomarker diagnoses or aids in the diagnosis of cancer.

In one embodiment, the above described methods of diagnosing or aiding in the diagnosis of cancer comprises detecting the expression of two or more biomarkers. In one embodiment, said two or more biomarkers are selected from the group consisting of: prolactin, MIF, OPN, IGF-II, E-Selectin, leptin, EGF, IL-17, MPIF-1, and IL-2sRa. In one embodiment, said two or more biomarkers are selected from the group consisting of: leptin, prolactin, OPN and IGF-II. In one embodiment, a significant difference in the expression of at least two or said two or more biomarkers diagnoses or aids in the diagnosis of cancer.

In one embodiment, the above described methods of diagnosing or aiding in the diagnosis of cancer comprises comparing the expression of three or more biomarkers. In one embodiment, said three or more biomarkers are selected from the group consisting of: leptin, prolactin, OPN and IGF-II. In one embodiment, a significant difference in the expression of said three or more biomarkers diagnoses or aids in the diagnosis of cancer.

In one embodiment, the above described methods of diagnosing or aiding in the diagnosis of cancer comprises comparing the expression of four or more biomarkers. In one embodiment, said four or more biomarkers include leptin, prolactin, OPN and IGF-II. In one embodiment, a significant difference in the expression of four or more biomarkers diagnoses or aids in the diagnosis of cancer.

In one embodiment, the expression of a biomarker is detected or measured using a reagent that detects said one or more biomarkers. In one embodiment, the reagent is an antibody or fragment thereof specific for said one or more biomarkers. In one embodiment, the reagent is directly or indirectly labeled with a detectable substance. In another embodiment, the expression of said one or more biomarker is detected using mass spectroscopy. In another embodiment, the expression of said one or more biomarker is detected by measuring the mRNA transcription levels of the gene encoding said one or more biomarker.

In another embodiment, the expression of said one or more biomarker is detected by: (a) detecting the expression of a polypeptide which is regulated by said one or more biomarker; (b) detecting the expression of a polypeptide which regulates said biomarker; or (c) detecting the expression of a metabolite of said biomarker.

In one embodiment, the sample used in the above described methods is a body fluid sample. In one embodiment, the body fluid sample is blood or serum.

The invention also comprises methods for monitoring the progression of cancer in a subject. In one embodiment, the invention comprises a method of monitoring the progression of cancer in a subject comprising comparing the expression of one or more biomarkers in a sample from a subject to the expression of said one or more biomarkers in a sample obtained from the subject at a subsequent point in time;

wherein said one or more biomarkers are selected from the group consisting of: 6Ckine, ACE, BDNF, CA125, E-Selectin, EGF, Eot2, ErbB1, follistatin, HCC4, HVEM, IGF-II, IGFBP-1, IL-17, IL-1srII, IL-2sRa, leptin, M-CSF R, MIF, MIP-1a, MIP3b, MMP-8, MMP7, MPIF-1, OPN, PARC, PDGF Rb, prolactin, ProteinC, TGF-b RIII, TNF-R1, TNF-a, VAP-1, VEGF R2 and VEGF R3; and wherein a difference in the expression of said one or more biomarker diagnoses or aids in the diagnosis of the progression of the cancer in the subject. In one embodiment, said one or more biomarkers are selected from the group consisting of: prolactin, MIF, OPN, IGF-II, E-Selectin, leptin, EGF, IL-17, MPIF-1, and IL-2sRa. In one embodiment, said one or more biomarkers are selected from the group consisting of: leptin, prolactin, OPN and IGF-II.

In one embodiment, the above described methods of monitoring the progression of cancer comprises comparing the expression of two or more biomarkers. In one embodiment, said two or more biomarkers are selected from the group consisting of: prolactin, MIF, OPN, IGF-II, E-Selectin, leptin, EGF, IL-17, MPIF-1, and IL-2sRa. In another embodiment, said two or more biomarkers are selected from the group consisting of: leptin, prolactin, OPN and IGF-II.

In one embodiment, the above described methods of monitoring the progression of cancer comprises comparing the expression of three or more biomarkers. In one embodiment, the above described methods of monitoring the progression of cancer comprises comparing the expression of four or more biomarkers. In one embodiment, the above described methods of monitoring the progression of cancer comprises comparing the expression of four or more biomarkers, wherein said four or more biomarkers include leptin, prolactin, OPN and IGF-II. In another embodiment, the above described method of monitoring the progression of cancer comprises comparing the expression of four biomarkers, wherein the four biomarkers are leptin, prolactin, OPN and IGF-II.

The invention also comprises methods for monitoring the effectiveness of a treatment against cancer. In one embodiment, the invention comprise a method for monitoring the effectiveness of a treatment against cancer comprising comparing the expression of one or more biomarkers in a sample from a subject prior to providing at least a portion of a treatment to the expression of said one or more biomarkers in a sample obtained from the subject after the subject has received at least a portion of the treatment; wherein said one or more biomarkers are selected from the group consisting of: 6Ckine, ACE, BDNF, CA125, E-Selectin, EGF, Eot2, ErbB1, follistatin, HCC4, HVEM, IGF-II, IGFBP-1, IL-17, IL-1srII, IL-2sRa, leptin, M-CSF R, MIF, MIP-1a, MIP3b, MMP-8, MMP7, MPIF-1, OPN, PARC, PDGF Rb, prolactin, ProteinC, TGF-b RIII, TNF-R1, TNF-a, VAP-1, VEGF R2 and VEGF R3; and wherein a difference in the expression of said one or more biomarker diagnoses or aids in the diagnosis of the efficacy of the treatment. In one embodiment, said one or more biomarkers are selected from the group consisting of: prolactin, MIF, OPN, IGF-II, E-Selectin, leptin, EGF, IL-17, MPIF-1, and IL-2sRa. In one embodiment, said one or more biomarkers are selected from the group consisting of: leptin, prolactin, OPN and IGF-II.

In one embodiment, the above described methods of monitoring the effectiveness of a treatment against cancer comprises comparing the expression of two or more biomarkers. In one embodiment, said two or more biomarkers are selected from the group consisting of: prolactin, MIF, OPN, IGF-II, E-Selectin, leptin, EGF, IL-17, MPIF-1, and IL-2sRa. In another embodiment, said two or more biomarkers are selected from the group consisting of: leptin, prolactin, OPN and IGF-II.

In one embodiment, the above described methods of monitoring the effectiveness of a treatment against cancer comprises comparing the expression of three or more biomarkers. In one embodiment, the above described methods of monitoring the effectiveness of a treatment against cancer comprises comparing the expression of four or more biomarkers. In one embodiment, the above described methods of monitoring the effectiveness of a treatment against cancer comprises comparing the expression of four or more biomarkers, wherein said four or more biomarkers include leptin, prolactin, OPN and IGF-II. In another embodiment, the above described method of monitoring the effectiveness of a treatment against cancer comprises comparing the expression of four biomarkers, wherein the four biomarkers are leptin, prolactin, OPN and IGF-II.

The invention also comprises kits for diagnosing or aiding in the diagnosis of cancer and kits for monitoring cancer. In one embodiment, the kit comprises: (i) a receptacle for receiving a sample; (ii) one or more reagents for detecting one or more biomarkers selected from the group consisting of: 6Ckine, ACE, BDNF, CA125, E-Selectin, EGF, Eot2, ErbB1, follistatin, HCC4, HVEM, IGF-II, IGFBP-1, IL-17, IL-1srII, IL-2sRa, leptin, M-CSF R, MIF, MIP-1a, MIP3b, MMP-8, MMP7, MPIF-1, OPN, PARC, PDGF Rb, prolactin, ProteinC, TGF-b RIII, TNF-R1, TNF-a, VAP-1, VEGF R2 and VEGF R3; and (iii) a reference sample. In one embodiment, the kit comprises one or more reagents for the detection of leptin, prolactin, OPN and IGF-II.

The invention also comprises a method to screen for a candidate compound useful to treat cancer. In one embodiment, the invention comprises a method to screen for a candidate compound useful to treat cancer comprising: (i) identifying a candidate compound which regulates the expression of at least one biomarker selected from the group consisting of: 6Ckine, ACE, BDNF, CA125, E-Selectin, EGF, Eot2, ErbB1, follistatin, HCC4, HVEM, IGF-II, IGFBP-1, IL-17, IL-1srII, IL-2sRa, leptin, M-CSF R, MIF, MIP-1a, MIP3b, MMP-8, MMP7, MPIF-1, OPN, PARC, PDGF Rb, prolactin, ProteinC, TGF-b RIII, TNF-R1, TNF-a, VAP-1, VEGF R2 and VEGF R3; and (ii) determining whether such candidate compound is effective to treat cancer. In one embodiment, the method comprises identifying a candidate compound which regulates the expression of at least one biomarkers selected from the group consisting of: prolactin, MIF, OPN, IGF-II, E-Selectin, leptin, EGF, IL-17, MPIF-1, and IL-2sRa. In one embodiment, the method comprises identifying a candidate compound which regulates the expression of at least one biomarkers selected from the group consisting of leptin, prolactin, OPN and IGF-II.

The invention also comprises a method of conducting a business. In one embodiment, the method of conducting a business comprises: (i) obtaining a sample; (ii) detecting the expression of one or more biomarker in the sample, wherein said one or more biomarkers are selected from the group consisting of: 6Ckine, ACE, BDNF, CA125, E-Selectin, EGF, Eot2, ErbB1, follistatin, HCC4, HVEM, IGF-II, IGFBP-1, IL-17, IL-1srII, IL-2sRa, leptin, M-CSF R, MIF, MIP-1a, MIP3b, MMP-8, MMP7, MPIF-1, OPN, PARC, PDGF Rb, prolactin, ProteinC, TGF-b RIII, TNF-R1, TNF-a, VAP-1, VEGF R2 and VEGF R3; and (iii) reporting the results of such detection. In one embodiment, said one or more biomarkers are selected from the group consisting of: prolactin, MIF, OPN, IGF-II, E-Selectin, leptin, EGF, IL-17, MPIF-1, and IL-2sRa. In another embodiment, said one or more biomarkers are selected from the group consisting of: leptin, prolactin, OPN and IGF-II.

In one embodiment, the invention comprises a method of conducting a business comprising: (i) obtaining a sample; (ii) detecting the expression of four biomarkers in the sample, wherein said four biomarkers leptin, prolactin, OPN and IGF-II; and (iii) reporting the results of such detection.

The invention also comprises methods to screen for candidate cancer biomarkers. In one embodiment, the invention comprises a method to screen for candidate cancer biomarkers comprising: (i) identifying a group of biomarkers that are potentially associated with cancer; (ii) comparing the level of expression of the biomarkers identified in step (i) in a first population of cancer subjects and in healthy subjects; (iii) selecting biomarkers exhibiting a significant difference in expression in said first population of cancer subjects; (iv) comparing the level of expression of the biomarkers identified in step (iii) in a second population of cancer subjects and in healthy subjects; and (v) selecting biomarkers exhibiting a significant difference in expression in said second population of cancer subjects; wherein the biomarkers identified in step (v) are candidate cancer biomarkers. In one embodiment, said first population of cancer subjects have newly diagnosed cancer, and said second population of cancer subjects have recurrent cancer. In one embodiment, said first population of cancer subjects have recurrent cancer and said second population of cancer subjects have newly diagnosed cancer. In another embodiment, wherein said first population of cancer subjects have late stage cancer and said second population of cancer subjects have early stage cancer. In another embodiment, said first population of cancer patients have early stage cancer and said second population of cancer subjects have later stage cancer. In another embodiment, said method further comprises: (vi) comparing the level of expression of the biomarkers identified in step (v) in a third population of cancer subjects and in healthy subjects, wherein the expression of said biomarkers is detected by using a different assay format; and (vii) selecting biomarkers exhibiting a significant different in expression in said third population of cancer subjects; wherein the biomarkers identified in step (vii) are candidate the biomarkers identified in step (v) or (vii) could distinguish between cancer and healthy subjects in a blind study.

The invention also comprises a method to screen for candidate cancer biomarkers comprising: (i) identifying a cancer biomarker; (ii) selecting polypeptides which regulate or are regulated by the biomarker identified in step (i); and (iii) measuring the expression of the polypeptides identified in step (ii) in cancer subjects and in healthy subjects, wherein a polypeptide which is differentially expressed in cancer subjects and in healthy subjects is a candidate cancer biomarker.

BRIEF DESCRIPTION OF THE DRAWINGS

FIG. 1 is a schematic representation of the screening process used to identify biomarkers which could discriminate between subjects with cancer and healthy subjects.

DETAILED DESCRIPTION OF THE INVENTION

I. Overview

Figure 2:
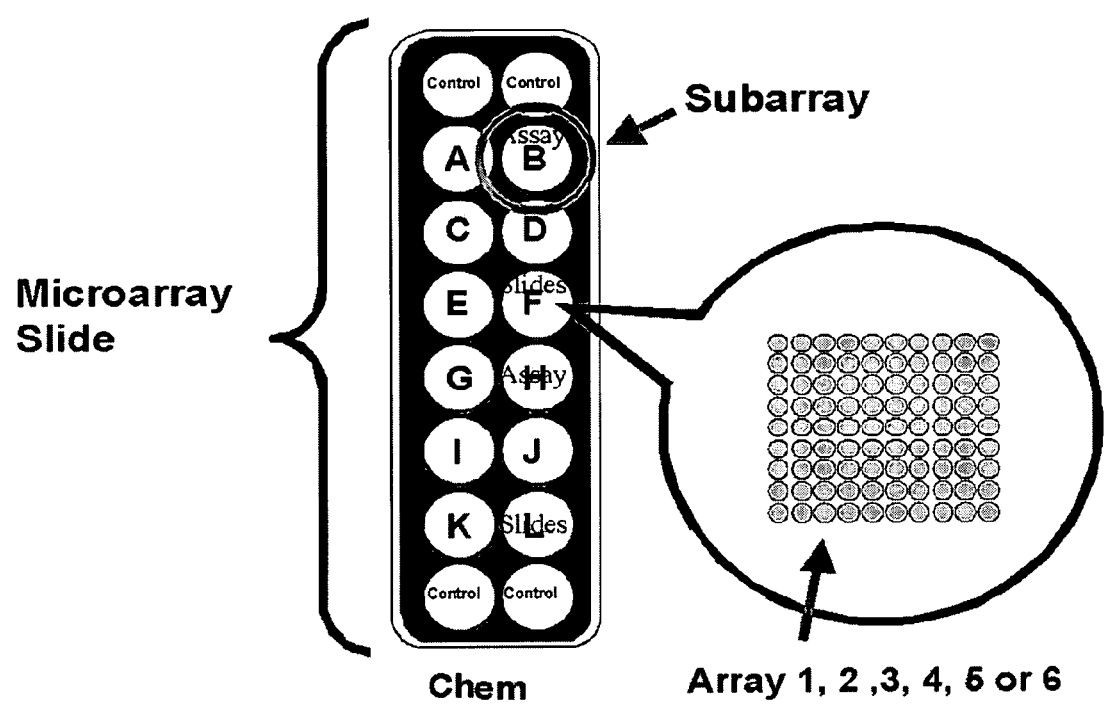
FIG. 2 is a schematic representation of a sample protein microarray slide with 16 subarrays. Subarrays refer to the 16 wells, or circular analysis sites, on the slide. Array refers to the antibody content printed in a well. Each microarray slide contains only one type of array.

Described herein is a method which can be used to discriminate between cancer subjects (including subjects diagnosed with early stage (stage I-II) disease) and healthy subjects. This method is based on the identification of biomarkers which are particularly well suited to discriminate between cancer subjects and healthy subjects. These biomarkers were identified using a unique and novel screening method described herein involving several different screening steps using samples from different subjects in each step and validation with different techniques. The biomarkers disclosed herein can be used in the diagnosis, prognosis and monitoring of cancer.

In one particular embodiment, the invention disclosed herein refers to a new test based on four biomarkers: leptin, prolactin, ORN and IGF II, which discriminate between cancer subjects and healthy subjects, particularly between ovarian cancer subjects and healthy subjects. In one embodiment, these four biomarkers can be used in a blood test for the diagriosis, prognosis and monitoring of ovarian cancer.

These biomarkers identified herein can be used in combination with additional known biomarkers. For example, a known biomarker of ovarian cancer is CA125. The use of CA125 in conjunction with the biomarkers identified herein presents a novel approach for the early detection of ovarian cancer and may significantly improve our ability to accurately detect pre-malignant change or early stage ovarian cancer in asymptomatic women at increased risk for the development of ovarian cancer. Further, the biomarkers identified in this application can be used in conjunction with other diagnostic techniques. For example, for the diagnosis of ovarian cancer, the biomarkers identified in this application can be used in conjunction with vaginal examination, ultrasound or MRI to diagnose ovarian cancer.

The articles "a," "an" and "the" are used herein to refer to one or to more than one (i.e., to at least one) of the grammatical object of the article.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably with, the phrase "such as but not limited to".

II. Methods of Diagnosis

In one embodiment, the invention refers to a method for diagnosing or aiding in the diagnosis of cancer in a subject. In one embodiment, the method comprises comparing the expression of one or more biomarkers selected from the group consisting of the biomarkers identified in Table 2 in a sample from a subject to a predetermined standard for each said one or more biomarkers, wherein a significant difference in the expression of said one or more biomarkers in said sample as compared to a predetermined standard of each said one or more biomarkers diagnoses or aids in the diagnosis of cancer. In one embodiment, said one or more biomarkers are selected from the group consisting of the biomarkers identified in Table 3. In another embodiment, said one or more biomarkers are selected from the group consisting of: leptin, prolactin, OPN and IGF-II.

When the biomarkers are prolactin and/or OPN, an increase in the expression of said biomarkers as compared to the predetermined standard for said biomarker diagnoses or aids in the diagnosis of cancer. When the biomarkers is leptin and/or IGF-II, a decrease in the expression of said biomarker as compared to the predetermined standard for said biomarker diagnoses or aids in the diagnoses of cancer. As used herein, an increase or decrease in expression refers to the fact that level of a gene expression product is made higher or lower, or to the fact that the activity of the gene expression product is enhanced or lowered.

The above described methods can be used to diagnose any cancer or tumor. In one embodiment, the cancer is ovarian cancer. In another embodiment, the cancer is breast cancer. In another embodiment, the cancer is colon cancer. In another embodiment, the cancer is prostate cancer. In another embodiment, the cancer is cervical cancer.

As used herein, the term "biomarker" refers to one or more polypeptides that can be used to: diagnose, or to aid in the diagnosis or prognosis of, cancer either alone or as combination of multiple polypeptides; monitor the progression of cancer; and/or monitor the effectiveness of a cancer treatment. As used herein, the term "polypeptide" refers to a polymer of amino acids, and not to a specific length. Thus, peptides, oligopeptides and proteins are included within the definition of polypeptide.

As used herein, the term "leptin" includes all homologs, naturally occurring allelic variants, isoforms and precursors of leptin. Leptin is also known as HGNC:6553, OB, OBS, obesity, or murine obesity homolog. In one embodiment, leptin comprises the amino acid sequence of Accession No. NP_000221 of the computerized storage and retrieval services dealing with information relating to nucleic acid sequence data owned by the United States Department of Health and Human Service, (Genbank™).

As used herein, the term "prolactin" includes all homologs, naturally occurring allelic variants, isoforms and precursors of prolactin. Prolactin is also known as PRL or HGNC:9445. In one embodiment, prolactin comprises the amino acid sequence of Accession No. NP_000939 of the computerized storage and retrieval service dealing with information relating to nucleic acid sequence data owned by the United States Department of Health and Human service (GenBank™).

As used herein, the term "OPN" includes all homologs, naturally occurring allelic variants, isoforms and precursors of OPN. OPN is also known as HGNC: 11255, BNSP, BSPI, ETA-1, secreted phosphoprotein-1 or osteopontin. In one embodiment, OPN comprises the amino acid sequence of Accession No. NP_000573 of the computerized storage and retrieval services dealing with information relating to nucleic acid sequence data owned by the United States Department of Health and Human Services, (GenBank™).

As used herein, the term "IGF-II" includes all homologs, naturally occurring allelic variants, isoforms and precursors of IGF-II. IGF-II is also known as HGNC:5466, insulin-like growth factor 2, insulin-like growth factor II or somatomedin A. In one embodiment, IGF-II comprises the amino acid sequence of Accession No. NP_000603 of the computerized storage and retrieval services dealing with information relating to nucleic acid sequence data owned by the United States Department of Health and Human Services (GenBank™).

As used herein, the term "subject" or "patient" includes all warm-blooded animals. In one embodiment the subject is a human. In one embodiment, the subject is a subject with an enhanced risk of developing cancer.

In one embodiment, when the method relates to ovarian cancer, the subject is a female (such as a woman) suspected of having or known to have ovarian cancer, or with an enhanced risk of developing ovarian cancer. For example, for ovarian cancer subjects having a familial history of ovarian cancer, subjects identified as having a mutant oncogene, and subjects at least about 50 years of age have an enhanced risk of developing ovarian cancer.

As used herein, the term "sample" refers to a material obtained from a subject. The sample can be derived from any biological source, including all body fluids (such as, for example, whole blood, plasma, serum, saliva, ocular lens fluid, sweat, urine, milk, etc.), tissue or extracts, cells, etc. Examples of ovary-associated body fluids include blood fluids (e.g. whole blood, blood serum, blood having platelets removed therefrom, etc.), lymph, ascitic fluids, gynecological fluids (e.g. ovarian, fallopian, and uterine secretions, menses, vaginal douching fluids, fluids used to rinse ovarian cell samples, etc.), cystic fluid, urine, and fluids collected by peritoneal rinsing (e.g. fluids applied and collected during laparoscopy or fluids instilled into and withdrawn from the peritoneal cavity of a human patient).

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

Expression of a biomarker of the invention may be assessed by any of a wide variety of well known methods for detecting expression of a transcribed molecule or its corresponding protein. Non-limiting examples of such methods include immunological methods for detection of secreted proteins, protein purification methods, protein function or activity assays, nucleic acid hybridization methods, nucleic acid reverse transcription methods, and nucleic acid amplification methods. In a preferred embodiment, expression of a marker gene is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a protein corresponding to the marker gene, such as the protein encoded by the open reading frame corresponding to the marker gene or such a protein which has undergone all or a portion of its normal post-translational modification. In another preferred embodiment, expression of a marker gene is assessed by preparing mRNA/cDNA (i.e. a transcribed polynucleotide) from cells in a patient sample, and by hybridizing the mRNA/cDNA with a reference polynucleotide which is a complement of a polynucleotide comprising the marker gene, and fragments thereof. cDNA can, optionally, be amplified using any of a variety of polymerase chain reaction methods prior to hybridization with the reference polynucleotide; preferably, it is not amplified.

As used herein, a "predetermined standard" for a biomarker refers to the levels of expression of said biomarker in healthy subjects or the expression levels of said biomarker in non-cancerous tissue from the same subject. The predetermined standard expression levels for a given biomarker can be established by prospective and/or retrospective statistical studies using only routine experimentation. Said predetermined standard expression levels can be determined by a person having ordinary skill in the art using well known methods.

The term "healthy subject" refers to a subject has not been diagnosed with cancer or who has not been diagnosed with cancer of the type which is being analyzed. Thus, for example, in a method to diagnose ovarian cancer, a "healthy subject" refers to a subject who does cancer or who does not have ovarian cancer.

As used herein, the term "significant difference" is well within the knowledge of a skilled artisan and will be determined empirically with reference to each particular biomarker. For example, a significant difference in the expression of a biomarker in a subject with cancer as compared to a healthy subject is any difference in expression which is statistically significant.

In one embodiment, the method comprises comparing the expression of two or more biomarkers and the diagnosis of cancer is based on a score-based classification method. In one embodiment, the score-based classification system is a based on binary numbers. In one embodiment, the score-based classification system comprises determining the expression of m different biomarkers; wherein each biomarker is assigned a score of 0 or 1, wherein a biomarker is assigned a score of 0 if the expression of said biomarker is not significantly different from the expression of said biomarker in a predetermined standard and wherein a biomarker is assigned a score of 1 if the expression of said biomarker is significantly different from the expression of said biomarker in a predetermined standard; wherein the subject is assigned an overall score which corresponds to the sum of the assigned scores from m different markers; and wherein a given threshold (t) is used to diagnose or aid in the diagnosis of cancer.

In one embodiment, the score-based classification system comprises comparing the expression of four (4) different biomarkers; wherein each biomarker is assigned a score of 0 or 1, wherein a biomarker is assigned a score of 0 if the expression of said biomarker is not significantly different from the expression of said biomarker in a predetermined standard and wherein a biomarker is assigned a score of 1 if the expression of said biomarker is significantly different from the expression of said biomarker in a predetermined standard; wherein the subject is assigned an overall score which corresponds to the sum of the assigned scores from four (4) different markers; and wherein a score or 2 or more diagnoses or aids in the diagnosis of cancer. In one embodiment, the four biomarkers are leptin, prolactin, OPN and IGF-II.

In one embodiment, the method comprises comparing the expression of two or more biomarkers, wherein the diagnosis of cancer is made by comparing the expression profile of said two or more biomarkers to a predetermined standard profile for said biomarkers, and wherein a difference in the profiles diagnoses or aids in the diagnosis of cancer. As used herein, an "expression profile" is a representation of the levels of expression of one or more biomarkers in a given sample.

In one embodiment, the predetermined standard profile is determined by comparing the expression of said two or more biomarkers in cancer subjects to the expression of said two or more biomarkers in healthy subjects using a machine learning technique. In one embodiment, the predetermined standard profile is determined by comparing the expression of said two or more biomarkers in cancer subjects and in healthy subjects using support vector machines, K-nearest neighbor classifier, or classification tree analysis.

In one embodiment, the method comprises detecting an additional known biomarker which is not identified in Table 2 and comparing the expression of said additional known biomarker to a predetermined standard for said additional known biomarker. Additional biomarkers for cancer can be identified by a person having ordinary skill in the art by reference to the published literature. In one embodiment, the cancer is ovarian cancer, and the additional biomarker for ovarian cancer is selected from the group consisting of: human stratum corneum chymotryptic enzyme (HSCCE), kallikrein 4, kallikrein 5, kallikrein 6 (protease M), kallikrein 8, kallikrein 9, kallikrein 10, CA125, CA15-3, CA19-9, OVX1, lysophosphatidic acid (LPA), carcinoebryonic antigen (CEA), macrophage colony-stimulating factor (M-CSF), prostasin, CA54-61, CA72, HMFG2, IL-6, IL-10, LSA, M-CSF, NB70K, PLAP, TAG72, TNF, TPA, UGTF, WAP four-disulfide core domain 2 (HE4), matrix metalloprotease 2, tetranectin, inhibin, mesothelyn, MUC1, VEGF, CLDN3, NOTCH3, E2F transcription factor 3 (E2F3), GTPase activating protein (RACGAP1), hemotological and neurological expressed 1 (HN1), apolipoprotein A1, laminin, claudin 3, claudin 4, tumor-associated calcium signal transducer 1 (TROP-1/Ep-CAM), tumor-associated calcium signal transducer 2 (TROP-2), ladinin 1, S100A2, SERPIN2 (PAI-2), CD24, lipocalin 2, matriptase (TADG-15), stratifin, transforming growth factor-beta receptor III, platelet-derived growth factor receptor alpha, SEMACAP3, ras homology gene family member I (ARHI), thrombospondin 2, disabled-2/differentially expressed in ovarian carcinoma 2 (Dab2/DOC2), and haptoglobin-alpha subunit. In another embodiment, the additional biomarker for ovarian cancer is the truncated form of transthyretin or the cleavage fragment of inter-alpha-trypsin inhibitor heavy chain H4 identified by Zhang et al., *Cancer Res.* 64(16):5882-90 (2004). In a preferred embodiment, the additional biomarker for ovarian cancer is CA125.

In one embodiment, the invention refers to a method for diagnosing or aiding in the diagnosis of cancer in a subject comprising comparing the expression of two or more biomarkers selected from the group consisting of the biomarkers identified in Table 2 in a sample from a subject to a predetermined standard for each said biomarker, wherein a significant difference in the expression of one or more biomarkers in said sample as compared to a predetermined standard of each biomarker diagnoses or aids in the diagnosis of cancer. In one embodiment, said two or more biomarkers are selected from the group consisting of the biomarkers identified in Table 3. In another embodiment, said two or more biomarkers are selected from the group consisting of: leptin, prolactin, OPN and IGF-II. In one embodiment, a significant difference in the expression of at least two of said two or more biomarkers diagnoses or aids in the diagnosis of cancer.

In one embodiment, the invention comprises to a method for diagnosing or aiding in the diagnosis of cancer in a subject comprising comparing the expression of three or more biomarkers selected from the group consisting of the biomarkers identified in Table 2 in a sample from a subject to a predetermined standard for each biomarker, wherein a significant difference in the expression of one or more biomarkers in said sample as compared to a predetermined standard of each said biomarker diagnoses or aids in the diagnosis of cancer. In one embodiment, said three or more biomarkers are selected from the group consisting of the biomarkers identified in Table 3. In another embodiment, said three or more biomarkers are selected from the group consisting of: leptin, prolactin, OPN and IGF-II. In one embodiment, a significant difference in the expression of at least two or said two or more biomarkers diagnoses or aids in the diagnosis of cancer.

In one embodiment, the invention refers to a method for diagnosing or aiding in the diagnosis of cancer in a subject comprising comparing the expression of four or more biomarkers selected from the group consisting of the biomarkers identified in Table 2 in a sample from a subject to a predetermined standard for each biomarker, wherein a significant difference in the expression of one or more biomarkers in said sample as compared to a predetermined standard of each said biomarker diagnoses or aids in the diagnosis of cancer. In one embodiment, said four or more biomarkers are selected from the group consisting of the biomarkers identified in Table 3. In another embodiment, said four or more biomarkers are selected from the group consisting of: leptin, prolactin, OPN and IGF-II. In one embodiment, a significant difference in the expression of at least two of said two or more biomarkers diagnoses or aids in the diagnosis of cancer.

The expression of said one or more biomarkers can be detected using any method known to a person having ordinary skill in the art. In one embodiment, the expression of said one or more biomarkers can be detected using a reagent that detects said one or more biomarkers. Said reagent can be any reagent that specifically detects said one or more biomarkers. Said reagent can be an antibody (natural or synthetic) or a fragment thereof specific for the biomarker, a peptide, a nucleic acid, or any other reagent that can specifically detect a biomarker. As used herein, the term "antibody" includes chimeric and synthetic antibodies, e.g., generated by combinatorial mutagenesis and phage display. The term "antibody" includes mimetics or peptidomimetics of antibodies. Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into non-peptide compounds with the activity of the parent peptides. For illustrative purposes, peptide analogs of the antibodies can be generated using, for example, benzodiazepines (e.g., see Freidinger et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988, p 123), C-7 mimics (Huffman et al. in *Peptides. Chemistry and Biology*, G. R. Marshall ed., ESCOM Publisher: Leiden, Netherlands, 1988, p. 105), keto-methylene pseudopeptides (Ewenson et al. (1986) *J. Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), β-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124: 141), and methyleneamino-modified (Roark et al. in *Peptides. Chemistry and Biology*, G. R. Marshall ed., ESCOM Publsiher: Leiden, Netherlands, 1988, p 134). Also, see generally, Session III: Analytic and synthetic methods, in *Peptides. Chemistry and Biology*, G. R. Marshall ed., ESCOM Publisher: Leiden, Netherlands, 1988).

In another embodiment, said reagent is directly or indirectly labeled with a detectable substance. The detectable substance may be, for example, selected, e.g., from a group consisting of radioisotopes, fluorescent compounds, enzymes, and enzyme co-factor. Methods of labeling antibodies are well known in the art.

As used herein, the term "detect", "detected" or "detecting" includes measure, measured or measuring.

The above described methods can be performed using any sample. In one embodiment, the sample is a body fluid sample. In one embodiment, the body fluid sample is blood or serum.

In another embodiment, the expression of said one or more biomarkers are detected using mass spectroscopy.

In yet another embodiment, the expression of said one or more biomarkers is detected by detecting the mRNA transcription levels of the gene encoding said at one or more biomarker.

In yet another embodiment, the expression of said one or more biomarkers can be detected by ELISA, RCA immunoassay, chemiluminescence, thin-film optical biosensor, proton resonance technology, protein microarray assay or any other detection method known in the art.

In one embodiment, the expression of said one or more biomarkers are detected by: (a) detecting the expression of a polypeptide which is regulated by said one or more biomarker; (b) detecting the expression of a polypeptide which regulates said biomarker; or (c) detecting the expression of a metabolite of said biomarker. A person of skill in the art would be able to identify polypeptides which regulate or are regulated by a biomarker, and metabolites of a biomarker, using only routine experimentation.

The above described methods to diagnose or aid in the diagnosis of cancer may be used in conjunction with other methods to validate the results (i.e. to more conclusively determine whether a subject has cancer). In one embodiment, the cancer is ovarian cancer and the above described methods further comprise: physical examination, ultrasound examination, x-ray examination, MRI examination, laparotomy and/or hematological tests. Hematological tests which may be indicative of ovarian cancer in a patient include analyses of serum levels of additional biomarkers of ovarian cancer.

III. Methods of Monitoring

In one embodiment, the invention comprises a method of monitoring the progression of cancer in a subject comprising comparing the expression of one or more biomarkers selected from the group consisting of the biomarkers identified in Table 2 in a sample from a subject; to the expression of said one or more biomarkers in a sample obtained from the subject at a subsequent point in time, wherein a difference in the expression of said one or more biomarkers are indicative of the progression of the cancer in the subject. In one embodiment, said one or more biomarkers are selected from the group consisting of the biomarkers identified in Table 3. In another embodiment, said one or more biomarkers are selected from the group consisting of leptin, prolactin, OPN and IGF-II.

In one embodiment, the method comprises comparing the expression of two or more biomarkers. In another embodiment, the method comprises comparing the expression of three or more biomarkers. In another embodiment, the method comprises comparing the expression of four or more biomarkers. In one embodiment, the method comprises comparing the expression of four or more biomarkers, wherein said four or more biomarkers include leptin, prolactin, OPN and IGF-II. In yet another embodiment, the method comprises comparing the expression of four biomarkers: leptin, prolactin, OPN and IGF-II.

In one embodiment, the method is used to monitor the progression of cancer after the subject has received a treatment for cancer.

The invention also comprises a method for monitoring the effectiveness of a treatment against cancer, comprising comparing the expression of one or more biomarkers selected from the group consisting of the biomarkers identified in Table 3 in a sample from a subject prior to providing at least a portion of a treatment to the expression of said one or more biomarkers in a sample obtained from the subject after the subject has received at least a portion of the treatment, wherein a difference in the expression of said one or more biomarkers are indicative of the efficacy of the treatment.

In one embodiment, said one or more biomarkers are selected from the group consisting of the biomarkers identified in Table 3. In another embodiment, said one or more biomarkers are selected from the group consisting of leptin, prolactin, OPN and IGF-II.

In one embodiment, the method comprises comparing the expression of two or more biomarkers. In another embodiment, the method comprises comparing the expression or three or more biomarkers. In another embodiment, the method comprises comparing the expression of four or more biomarkers. In one embodiment, the method comprises comparing the expression of four or more biomarkers, wherein said four or more biomarkers include leptin, prolactin, OPN and IGF-II. In yet another embodiment, the method comprises comparing the expression of four biomarkers: leptin, prolactin, OPN and IGF-II.

It will be appreciated that as used herein, the "treatment" may be any treatment for treating ovarian cancer including, but not limited to, chemotherapy, immunotherapy, gene therapy, radiation therapy and surgical removal of tissue. As used herein, "a portion of a treatment" refers to any portion of a treatment for cancer, such as a dose of a compound used to treat cancer, or a portion of a treatment such as chemotherapy.

The above described methods of monitoring cancer are applicable to any cancer or tumor. In one embodiment, the method is for monitoring ovarian cancer. In one embodiment, the method is for the monitoring breast cancer. In one embodiment, the method is for monitoring colon cancer. In another embodiment, the method is for monitoring cervical cancer.

IV. Kits

The invention also comprises kits for diagnosing or aiding in the diagnosis of cancer or for monitoring cancer. The kits can be used to diagnose or monitor any cancer. In one embodiment, the kit is for the diagnosis or monitoring of ovarian cancer. In one embodiment, the kit is for the diagnosis or monitoring of breast cancer. In one embodiment, the kit is for the diagnosis or monitoring of colon cancer. In one embodiment, the kit is for the diagnosis or monitoring of cervical cancer.

In one embodiment, the kit comprises: (i) a receptacle for receiving a sample; (ii) one or more reagents for detecting one or more biomarkers selected from the group consisting of the biomarkers identified in Table 2; and (iii) a reference sample. In one embodiment, the kit comprises one or more reagents for detecting one or more biomarkers selected from the group consisting of the biomarkers identified in Table 3. In one embodiment, the kit comprises one or more reagents for detecting one or more biomarkers selected from the group consisting of leptin, prolactin, OPN and IGF-II.

In one embodiment, the kit comprises reagents for detecting two or more biomarkers. In one embodiment, said two or more biomarkers are selected from the group consisting of: leptin, prolactin, OPN and IGF-II.

In another embodiment, said kit comprises reagents for detecting three or more biomarkers.

In one embodiment, the kit comprises reagents for detecting four or more biomarkers. In one embodiment, said four or more biomarkers include leptin, prolactin, OPN and IGF-II.

The reagents may be labeled compounds or agents capable of detecting a polypeptide or an mRNA encoding a polypeptide corresponding to a marker gene of the invention in a biological sample and means for determining the amount of the polypeptide or mRNA in the sample (e.g., an antibody which binds the polypeptide or an oligonucleotide probe which binds to DNA or mRNA encoding the polypeptide). Suitable reagents for binding with a polypeptide corresponding to a marker gene of the invention include antibodies, antibody derivatives, antibody fragments, and the like. Suitable reagents for binding with a nucleic acid (e.g. a genomic DNA, an mRNA, a spliced mRNA, a cDNA, or the like) include complementary nucleic acids.

For antibody-based kits, the kit can comprise, for example: (1) a first antibody (e.g., attached to a solid support) which binds to a polypeptide corresponding to a marker gene of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker gene of the invention or (2) a pair of primers useful for amplifying a nucleic acid molecule corresponding to a marker gene of the invention.

The reference sample is used to compare the results obtained from the sample being tested.

The kit can also comprise other components such as a buffering agent, a preservative, or a protein stabilizing agent. The kit can further comprise components necessary for detecting the detectable label (e.g., an enzyme or a substrate).

Each component of the kit can be enclosed within an individual container and all of the various containers can be within a single package, along with instructions for interpreting the results of the assays performed using the kit.

V. Screening Methods

The present invention also comprises methods to screen for candidate compounds useful to treat cancer. In one embodiment, the invention comprises a method to screen for a candidate compound useful to treat cancer comprising: (i) identifying a candidate compound which regulates the expression of one or more biomarkers selected from the group consisting of the biomarkers identified in Table 2; and (ii) determining whether such candidate compound is effective to treat cancer. In one embodiment, said one or more biomarkers are selected from the group consisting of the biomarkers identified in Table 3. In another embodiment, said one or more biomarkers are selected from the group consisting of leptin, prolactin, OPN and IGF-II.

In one embodiment, the invention comprises a method to screen for a candidate compound useful to treat cancer comprising: (i) identifying a candidate compound which regulates the expression of two or more biomarkers selected from the group consisting of the biomarkers identified in Table 2; and (ii) determining whether such candidate compound is effective to treat cancer. In one embodiment, said two or more biomarkers are selected from the group consisting of the biomarkers identified in Table 3. In another embodiment, said two or more biomarkers are selected from the group consisting of leptin, prolactin, OPN and IGF-II.

The present invention also comprises methods to screen for candidate compounds useful to treat cancer. In one embodiment, the invention comprises a method to screen for a candidate compound useful to treat cancer comprising: (i) identifying a candidate compound which regulates the expression of three or more biomarkers selected from the group consisting of the biomarkers identified in Table 2; and (ii) determining whether such candidate compound is effective to treat cancer. In one embodiment, said three or more biomarkers are selected from the group consisting of the biomarkers identified in Table 3. In another embodiment, said three or more biomarkers are selected from the group consisting of leptin, prolactin, OPN and IGF-II.

The present invention also comprises methods to screen for candidate compounds useful to treat cancer. In one embodiment, the invention comprises a method to screen for a candidate compound useful to treat cancer comprising: (i) identifying a candidate compound which regulates the expression of four or more biomarkers selected from the group consisting of the biomarkers identified in Table 2; and (ii) determining whether such candidate compound is effective to treat cancer. In one embodiment, said four or more biomarkers are selected from the group consisting of the biomarkers identified in Table 3. In another embodiment, said four or more biomarkers include leptin, prolactin, OPN and IGF-II.

As used herein, the term "compound" refers to any chemical entity, pharmaceutical, drug, and the like that can be used to treat or prevent a disease, illness, conditions, or disorder of bodily function. Compounds comprise both known and potential therapeutic compounds. A compound can be determined to be therapeutic by screening using the screening methods of the present invention. Examples of test compounds include, but are not limited to peptides, polypeptides, synthetic organic molecules, naturally occurring organic molecules, nucleic acid molecules, and combinations thereof.

The above described screening methods can be used to screen for candidate compounds useful to treat any cancer. In one embodiment, the method is to screen for candidate compounds useful to treat ovarian cancer. In another embodiment, the method is to screen for candidate compounds useful to treat breast cancer. In another embodiment, the method is to screen for candidate compounds useful to treat colon cancer. In another embodiment, the method is to screen for candidate compounds useful to treat cervical cancer.

VI. Business Methods

The invention further comprises a method of conducting a business comprising: (i) obtaining a sample; (ii) detecting the expression of at least one biomarker in the sample, wherein said one or more biomarker is selected from the group consisting of the biomarkers identified in Table 2; and (iii) reporting the results of such detection. In one embodiment, said one or more biomarkers are selected from the group consisting of the biomarkers identified in Table 3. In another embodiment, said one or more biomarkers are selected from the group consisting of leptin, prolactin, OPN and IGF-II.

The invention further comprises a method of conducting a business comprising: (i) obtaining a sample; (ii) detecting the expression of leptin, prolactin, OPN and IGF-II; and (iii) reporting the results of such detection.

VII. General Screening Methods

The invention also comprises a method to screen for candidate cancer biomarkers comprising: (i) identifying a group of biomarkers that are potentially associated with cancer (such as oncogenes, tumor suppressor genes, growth factor-like genes, protease-like genes, and protein kinase-like genes); (ii) comparing the level of expression of the biomarkers identified in step (i) in a first population of cancer subjects and in healthy subjects; (iii) selecting biomarkers exhibiting a significant difference in expression in said first population of cancer subjects; (iv) comparing the level of expression of the biomarkers identified in step (iii) in a second population of cancer subjects and in healthy subjects; and (v) selecting biomarkers exhibiting a significant difference in expression in said second population of cancer subjects; wherein the biomarkers identified in step (v) are candidate cancer biomarkers. The first population of cancer subjects and the second population of cancer subjects may be any two cancer populations so long as the two populations are different. In one embodiment, said first population of cancer subjects consists of subjects newly diagnosed with cancer, and said second population of cancer subjects consists of subjects having recurrent cancer. In another embodiment, said first population of cancer subjects consists of subjects having later stage cancer and said second population of cancer subjects consists of subjects having early stage cancer; or where said first population of cancer patients consists of subjects having early stage cancer and said second population of cancer subjects consists of subjects having later stage cancer.

A person of skill in the art would be able to identify biomarkers which are potentially associated with cancer. Such biomarkers can be selected from the group consisting of as oncogenes, tumor suppressor genes, growth factor-like genes, protease-like genes, and protein kinase-like genes.

In one embodiment, the method further comprises: (vi) comparing the level of expression of the biomarkers identified in step (v) in a third population of cancer subjects and in healthy subjects, wherein the expression of said biomarkers is detected by using a different assay format; and (vi) selecting biomarkers exhibiting a significant different in expression in said third population of cancer patients; wherein the biomarkers identified in step (vii) are candidate biomarkers for cancer. Thus, for example, in one embodiment, the expression of said biomarker is first detected using a high throughput assay, and then detected using an assay that is specific for the protein in question. For example, in one embodiment, the expression of said biomarker is first detected by using RCA microarray immunoassay and then detected by ELISA assay. The third population of cancer subjects may be the same or different from the first and second population of cancer subjects.

In one embodiment, the method further comprises determining whether the biomarkers identified in step (v) or (vii) could distinguish between cancer and healthy subjects in a blind study. The results of the blind assay can be analyzed using well known statistical methods.

The expression of said biomarkers can be compared using any method known in the art. In one embodiment, the expression of the biomarkers is detected using protein array, mass spectroscopy, gel electrophoresis or an immunoassay. In one embodiment, the expression of the biomarkers is detected using RCA microarray immunoassay. In another embodiment, the expression of the biomarkers is measured using ELISA. These methods are well known in the art.

The invention also comprise a method to screen for candidate cancer biomarkers comprising: (i) identifying a cancer biomarker; (ii) selecting polypeptides which regulate or are regulated by the biomarker identified in step (i); and (iii) measuring the expression of the polypeptides identified in step (ii) in cancer subjects and in healthy subjects, wherein a polypeptide which is differentially expressed in cancer subjects and in healthy subjects is a candidate cancer biomarker.

The above described screening methods can be used to screen for candidate biomarkers of any cancer. In one embodiment, the method is to screen for candidate compounds useful to treat ovarian cancer. In another embodiment, the method is to screen for candidate biomarkers of breast cancer. In another embodiment, the method is to screen for candidate biomarkers of colon cancer. In another embodiment, the method is to screen for candidate biomarkers of cervical cancer.

EXEMPLIFICATION

Example 1

The Identification of Biomarkers of Ovarian Cancer

FIG. 1 is a schematic representation of the novel screening assay used to identify biomarkers of ovarian cancer which can be used to distinguish subjects with ovarian cancer and healthy subjects. As shown in FIG. 1, during Phase I of the screening method, the levels of expression of 169 proteins were measured in 46 serum samples (18 samples were obtained from subjects with ovarian cancer and 28 samples were obtained from healthy, age-matched controls) via RCA immunoassay microarray in order to identify proteins that are differentially expressed in subjects with ovarian cancer and in healthy subjects.

TABLE 1

Proteins (analytes) used to screen for biomarkers of ovarian cancer. (As used herein, the tern "analyte" refers to a molecule or compound, such as a polypeptide or nucleic acid, whose presence is to be identified in a sample.)

| | Protein (abbr.) | Protein (full name) |
|---|---|---|
| | Array 1 analytes | |
| 1 | ANG | Angiogenin |
| 2 | BLC (BCA-1) | B-lymphocyte chemoattractant |
| 3 | EGF | Epidermal growth factor |
| 4 | ENA-78 | Epithelial cell-derived neutrophil-activating peptide |
| 5 | Eot | Eotaxin |
| 6 | Eot-2 | Eotaxin-2 |
| 7 | Fas | Fas (CD95) |
| 8 | FGF-7 | Fibroblast growth factor-7 |
| 9 | FGF-9 | Fibroblast growth factor-9 |
| 10 | GDNF | Glial cell line derived neurotrophic factor |
| 11 | GM-CSF | Granulocyte macrophage colony stimulating factor |
| 12 | IL-1ra | Interleukin 1 receptor antagonist |
| 13 | IL-2 sRα | Interleukin 2 soluble receptor alpha |
| 14 | IL-3 | Interleukin 3 |
| 15 | IL-4 | Interleukin 4 |
| 16 | IL-5 | Interleukin 5 |
| 17 | IL-6 | Interleukin 6 |
| 18 | IL-7 | Interleukin 7 |
| 19 | IL-8 | Interleukin 8 |
| 20 | IL-13 | Interleukin 13 |
| 21 | IL-15 | Interleukin 15 |
| 22 | MCP-2 | Monocyte chemotactic protein 2 |
| 23 | MCP-3 | Monocyte chemotactic protein 3 |
| 24 | MIP-1α | Macrophage inflammatory protein 1 alpha |
| 25 | MPIF | Myeloid progenitor inhibitory factor 1 |
| 26 | OSM | Oncostatin M |
| 27 | PIGF | Placental growth factor |
| | Array 2 analytes | |
| 1 | AR | Amphiregulin |
| 2 | BDNF | Brain-derived neurotrophic factor |
| 3 | Flt-3 Lig | fms-like tyrosine kinase-3 ligand |
| 4 | GCP-2 | Granulocyte chemotactic protein 2 |
| 5 | HCC4 (NCC4) | Hemofiltrate CC chemokine 4 |
| 6 | I-309 | I-309 |
| 7 | IL-1α | Interleukin 1 alpha |
| 8 | IL-1β | Interleukin 1 beta |
| 9 | IL-2 | Interleukin 2 |
| 10 | IL-17 | Interleukin 17 |
| 11 | MCP-1 | Monocyte chemotactic protein 1 |
| 12 | M-CSF | Macrophage colony stimulating factor |
| 13 | MIG | Monokine induced by interferon gamma |
| 14 | MIP-1β | Macrophage inflammatory protein 1 beta |

TABLE 1-continued

Proteins (analytes) used to screen for biomarkers of ovarian cancer. (As used herein, the term "analyte" refers to a molecule or compound, such as a polypeptide or nucleic acid, whose presence is to be identified in a sample.)

| | Protein (abbr.) | Protein (full name) |
|---|---|---|
| 15 | MIP-1δ | Macrophage inflammatory protein 1 delta |
| 16 | NT-3 | Neurotrophin 3 |
| 17 | NT-4 | Neurotrophin 4 |
| 18 | PARC | Pulmonary and activation-regulated chemokine |
| 19 | RANTES | Regulated upon activation, normal T expressed and presumably secreted |
| 20 | SCF | Stem cell factor |
| 21 | sgp130 | Soluble glycoprotein 130 |
| 22 | TARC | Thymus and activation regulated chemokine |
| 23 | TNF-RI | Tumor necrosis factor receptor I |
| 24 | TNF-α | Tumor necrosis factor alpha |
| 25 | TNF-β | Tumor necrosis factor beta |
| 26 | VEGF | Vascular endothelial growth factor |

Array 3 analytes

| | Protein (abbr.) | Protein (full name) |
|---|---|---|
| 1 | BTC | Betacellulin |
| 2 | DR6 | Death receptor 6 |
| 3 | Fas Lig | Fas ligand |
| 4 | FGF acid (FGF-1) | Fibroblast growth factor acidic |
| 5 | Fractalkine | Fractalkine |
| 6 | GRO-β | Growth related oncogene beta |
| 7 | HCC-1 | Hemofiltrate CC chemokine 1 |
| 8 | HGF | Hepatocyte growth factor |
| 9 | HVEM | Herpes virus entry mediator |
| 10 | ICAM-3 (CD50) | Intercellular adhesion molecule 3 |
| 11 | IGFBP-2 | Insulin-like growth factor binding protein 2 |
| 12 | IL-2 Rγ | Interleukin 2 receptor gamma |
| 13 | IL-5 Rα (CD125) | Interleukin 5 receptor alpha |
| 14 | IL-9 | Interleukin 9 |
| 15 | Leptin/OB | Leptin |
| 16 | L-Selectin (CD62L) | Leukocyte selectin |
| 17 | MCP-4 | Monocyte chemotactic protein 4 |
| 18 | MIP-3β | Macrophage inflammatory protein 3 beta |
| 19 | MMP-7 (total) | Matrix metalloproteinase 7 |
| 20 | MMP-9 | Matrix metalloproteinase 9 |
| 21 | PECAM-1 (CD31) | Platelet endothelial cell adhesion molecule-1 |
| 22 | RANK | Receptor activator of NF-kappa-B |
| 23 | SCF R | Stem cell factor receptor |
| 24 | TIMP-1 | Tissue inhibitors of metalloproteinases 1 |
| 25 | TRAIL R4 | TNF-related apoptosis-inducing ligand receptor 4 |
| 26 | VEGF-R2 (Flk-1/KDR) | Vascular endothelial growth factor receptor 2 |
| 27 | ST2 | Interleukin 1 receptor 4 |

Array 4 analytes

| | Protein (abbr.) | Protein (full name) |
|---|---|---|
| 1 | ALCAM | Activated leukocyte cell adhesion molecule |
| 2 | β-NGF | beta-nerve growth factor |
| 3 | CD27 | CD27 |
| 4 | CTACK | Cutaneous T-cell attracting chemokine |
| 5 | CD30 | CD30 |
| 6 | Eot-3 | Eotaxin-3 |
| 7 | FGF-2 | Fibroblast growth factor-2 (FGF-basic) |
| 8 | FGF-4 | Fibroblast growth factor-4 |
| 9 | Follistatin | Follistatin |
| 10 | GRO-γ | Growth related oncogene gamma |
| 11 | ICAM-1 | Intercellular adhesion molecule 1 |
| 12 | IFN-γ | Interferon gamma |
| 13 | IFN-ω | Interferon omega |
| 14 | IGF-1R | Insulin-like growth factor I receptor |
| 15 | IGFBP-1 | Insulin-like growth factor binding protein 1 |
| 16 | IGFBP-3 | Insulin-like growth factor binding protein 3 |
| 17 | IGFBP-4 | Insulin-like growth factor binding protein 4 |
| 18 | IGF-II | Insulin-like growth factor II |
| 19 | IL-1 sR1 | Interleukin 1 soluble receptor I |
| 20 | IL-1 sRII | Interleukin 1 soluble receptor II |
| 21 | IL-10 Rβ | Interleukin 10 receptor beta |
| 22 | IL-16 | Interleukin 16 |
| 23 | IL-2 Rβ | Interleukin 2 receptor beta |
| 24 | I-TAC | Interferon gamma-inducible T cell alpha chemoattractant |
| 25 | Lptn | Lymphotactin |
| 26 | LT βR | lymphotoxin-beta receptor |
| 27 | M-CSF R | Macrophage colony stimulating factor receptor |
| 28 | MIP-3α | Macrophage inflammatory protein 3 alpha |
| 29 | MMP-10 | Matrix metalloproteinase 10 |

TABLE 1-continued

Proteins (analytes) used to screen for biomarkers of ovarian cancer. (As used herein, the term "analyte" refers to a molecule or compound, such as a polypeptide or nucleic acid, whose presence is to be identified in a sample.)

| | Protein (abbr.) | Protein (full name) |
|---|---|---|
| 30 | PDGF Rα | Platelet-derived growth factor receptor alpha |
| 31 | PF4 | Platelet factor-4 |
| 32 | sVAP-1 | Soluble Vascular Adhesion Protein-1 |
| 33 | TGF-α | Transforming growth factor alpha |
| 34 | TIMP-2 | Tissue inhibitors of metalloproteinases 2 |
| 35 | TRAIL R1 | TNF-related apoptosis-inducing ligand receptor 1 |
| 36 | VE-cadherin | Vascular Endothelial Cadherin |
| 37 | VEGF-D | Vascular endothelial growth factor-D |

Array 5 analytes

| | | |
|---|---|---|
| 1 | 4-1BB (CD137) | 4-1BB |
| 2 | ACE-2 | Angiotensin I converting enzyme-2 |
| 3 | AFP | Alpha fetoprotein |
| 4 | AgRP | Agouti-related protein |
| 5 | CD141 | Thrombomodulin/CD141 |
| 6 | CD40 | CD40 |
| 7 | CNTF Rα | Ciliary neurotrophic factor receptor alpha |
| 8 | CRP | C-reactive protein |
| 9 | D-Dimer | D-Dimer |
| 10 | E-Selectin | E-selectin |
| 11 | HCG | Human chorionic gonadotrophin |
| 12 | IGFBP-6 | Insulin-like Growth Factor Binding Protein 6 |
| 13 | IL-12 (p40) | Interleukin 12 p40 |
| 14 | IL-18 | Interleukin 18 |
| 15 | LIF Rα (gp190) | Leukemia inhibitory factor soluble receptor alpha |
| 16 | MIF | Macrophage migration inhibitory factor |
| 17 | MMP-8 (total) | Matrix Metalloproteinase-8 |
| 18 | NAP-2 | Neutrophil Activating Peptide 2 |
| 19 | Neutrophil elastase | Neutrophil elastase |
| 20 | PAI-II | Plasminogen activator inhibitor-II |
| 21 | Prolactin | Prolactin |
| 22 | Protein C | Human Protein C |
| 23 | Protein S | Human Protein S |
| 24 | P-Selectin | P-Selectin |
| 25 | TSH | Thyroid stimulating hormone |

Array 6 analytes

| | | |
|---|---|---|
| 1 | 6Ckine | 6Ckine |
| 2 | ACE | Angiotensin converting enzyme |
| 3 | CA 125 | Cancer antigen 125 |
| 4 | CNTF | Ciliary neurotrophic factor |
| 5 | Endostatin | Endostatin |
| 6 | Endothelin 3 | Endothelin 3 |
| 7 | ErbB1 | Epidermal growth factor receptor 1 |
| 8 | ErbB2 | Epidermal growth factor receptor 2 |
| 9 | FGF R3 (IIIc) | Fibroblast growth factor receptor 3 IIIc isoform |
| 10 | FGF-6 | Fibroblast growth factor-6 |
| 11 | FGF-R3 (IIIb) | Fibroblast growth factor receptor 3 IIIb isoform |
| 12 | G-CSF | Granulocyte colony stimulating factor |
| 13 | HB-EGF | Heparin-Binding EGF-like Growth Factor |
| 14 | IFN-a | Interferon alpha |
| 15 | LIF | Leukemia inhibitory factor |
| 16 | MMP-1 | Matrix metalloproteinase 1 |
| 17 | MMP-2 | Matrix metalloproteinase 2 |
| 18 | Osteopontin | Osteopontin |
| 19 | PAI-1 | Plasminogen activator inhibitor type 1 |
| 20 | PDGF Rb | Platelet-derived growth factor receptor beta |
| 21 | PEDF | Pigment epithelium-derived factor |
| 22 | sVCAM-1 | Soluble VCAM-1 |
| 23 | TGF-b RIII | Transforming growth factor beta receptor III |
| 24 | Tie-2 | Tyrosine kinase with Ig and EGF homology domains 2 |
| 25 | uPA | Urokinase plasminogen activator |
| 26 | uPAR | Urokinase plasminogen activator receptor |
| 27 | VEGF R3 | VEGF receptor 3 |

From this group of 169 proteins, 35 proteins were identified which were differentially expressed between healthy subjects and subjects with ovarian cancer (p-values less than 0.05 based on analysis of variance tests (ANOVA)). This data is identified in Table 2.

TABLE 2

Proteins showing a significant (p < 0.05) difference in expression between subjects with ovarian cancer and healthy subjects.

| Protein | Healthy Subjects | | | Ovarian Cancer | | | Healthy-Ovarian Cancer | | | |
|---|---|---|---|---|---|---|---|---|---|---|
| | Mean | Std Dev | N | Mean | Std Dev | N | Mean | Std Dev | EffSize | p-value |
| 6Ckine | 9.18 | 0.52 | 28 | 9.67 | 0.69 | 51 | −0.49 | 0.64 | −0.76 | 0.001813 |
| ACE | 12.09 | 0.43 | 28 | 11.67 | 0.61 | 51 | 0.42 | 0.56 | 0.76 | 0.001763 |
| BDNF | 13.7 | 0.92 | 28 | 12.82 | 1.21 | 51 | 0.88 | 1.12 | 0.79 | 0.001293 |
| CA125 | 7.05 | 0.42 | 28 | 11.3 | 2.45 | 51 | −4.25 | 1.99 | −2.13 | <.000001 |
| E-Selectin | 13.83 | 0.62 | 28 | 13.4 | 0.76 | 51 | 0.44 | 0.71 | 0.61 | 0.011176 |
| EGF | 8.41 | 1.63 | 28 | 10.14 | 1.57 | 51 | −1.73 | 1.59 | −1.09 | 0.000015 |
| Eot2 | 13.12 | 1.11 | 28 | 12.55 | 1.2 | 51 | 0.57 | 1.17 | 0.49 | 0.04228 |
| ErbB1 | 11.79 | 0.39 | 28 | 11.36 | 0.55 | 51 | 0.44 | 0.5 | 0.87 | 0.000383 |
| Follistatin | 10.26 | 0.63 | 28 | 10.76 | 1.02 | 51 | −0.49 | 0.9 | −0.55 | 0.0225 |
| HCC4 | 13.93 | 0.59 | 28 | 14.17 | 0.45 | 51 | −0.25 | 0.5 | −0.49 | 0.04178 |
| HVEM | 8.33 | 0.67 | 28 | 8.75 | 0.7 | 51 | −0.42 | 0.69 | −0.61 | 0.011777 |
| IGF-II | 13.53 | 0.46 | 28 | 13.04 | 0.53 | 51 | 0.49 | 0.51 | 0.97 | 0.000094 |
| IGFBP-1 | 13.24 | 1.58 | 28 | 13.97 | 1.34 | 51 | −0.73 | 1.43 | −0.51 | 0.033016 |
| IL-17 | 8.78 | 0.56 | 28 | 8.24 | 0.55 | 51 | 0.53 | 0.55 | 0.96 | 0.000105 |
| IL-1srII | 9.96 | 0.6 | 28 | 9.48 | 0.69 | 51 | 0.48 | 0.66 | 0.72 | 0.002983 |
| IL-2sRa | 13.14 | 0.67 | 27 | 13.77 | 0.57 | 51 | −0.63 | 0.6 | −1.04 | 0.00004 |
| Leptin | 12.77 | 1.62 | 27 | 10.83 | 2.78 | 51 | 1.94 | 2.44 | 0.79 | 0.00134 |
| M-CSF R | 12.98 | 0.35 | 28 | 12.78 | 0.37 | 51 | 0.19 | 0.37 | 0.53 | 0.027136 |
| MIF | 10.75 | 0.75 | 28 | 11.82 | 0.75 | 51 | −1.07 | 0.75 | −1.42 | <.000001 |
| MIP-1a | 6.85 | 0.69 | 28 | 6.45 | 0.73 | 51 | 0.4 | 0.71 | 0.56 | 0.020757 |
| MIP3b | 7.55 | 0.73 | 28 | 7.92 | 0.8 | 51 | −0.37 | 0.77 | −0.48 | 0.043303 |
| MMP-8 | 13.92 | 1.03 | 28 | 14.53 | 0.82 | 51 | −0.61 | 0.9 | −0.68 | 0.004956 |
| MMP7 | 11.57 | 0.48 | 28 | 12 | 0.58 | 51 | −0.43 | 0.55 | −0.79 | 0.001262 |
| MPIF-1 | 9.27 | 0.6 | 28 | 9.9 | 0.7 | 51 | −0.63 | 0.67 | −0.94 | 0.000155 |
| OPN | 12.62 | 0.79 | 28 | 13.81 | 0.69 | 51 | −1.2 | 0.73 | −1.64 | <.000001 |
| PARC | 14.21 | 0.2 | 28 | 14.38 | 0.23 | 51 | −0.17 | 0.22 | −0.78 | 0.001318 |
| PDGF Rb | 10.74 | 0.97 | 28 | 10.13 | 1.13 | 50 | 0.61 | 1.08 | 0.56 | 0.019795 |
| Prolactin | 11.01 | 0.51 | 28 | 11.75 | 1.12 | 51 | −0.74 | 0.95 | −0.78 | 0.001445 |
| ProteinC | 13.59 | 0.31 | 28 | 13.24 | 0.38 | 51 | 0.35 | 0.36 | 0.97 | 0.000089 |
| TGF-b RIII | 10.46 | 1.15 | 28 | 11.46 | 1.12 | 51 | −1 | 1.13 | −0.88 | 0.000344 |
| TNF-R1 | 10.14 | 1.23 | 28 | 10.73 | 1.18 | 50 | −0.59 | 1.2 | −0.5 | 0.039197 |
| TNF-a | 7.06 | 0.97 | 28 | 6.3 | 0.7 | 51 | 0.75 | 0.8 | 0.94 | 0.000152 |
| VAP-1 | 14.06 | 0.28 | 24 | 13.78 | 0.65 | 44 | 0.29 | 0.55 | 0.52 | 0.042888 |
| VEGF R2 | 8.84 | 0.38 | 28 | 8.59 | 0.49 | 51 | 0.26 | 0.46 | 0.56 | 0.0189 |
| VEGF R3 | 10 | 0.55 | 28 | 9.51 | 0.67 | 51 | 0.49 | 0.63 | 0.78 | 0.001388 |

The protein (or analytes) identified in Table 2 are also known by other names, which can be identified by reference to the full name of the protein as described in Table 1 and by reference to the published literature. One way of identifying other names for the proteins identified in Table 2 is by reference to the various NCBI databases, which include the computerized storage and retrieval services dealing with information relating to nucleic acid sequence data owned by the United States Department of Health and Human Services (GenBank™).

These 35 proteins were selected for further characterization with 40 serum samples obtained from subjects with recurrent ovarian cancer. From this group of 35 proteins, ten (10) biomarkers exhibited the greatest differences in protein expression between subjects with recurrent ovarian cancer and healthy subjects. These 10 biomarkers are identified in Table 3.

TABLE 3

Proteins showing significant difference in expression between subjects with recurrent ovarian cancer and healthy subjects.

| Protein | Bonferroni adjusted p-value |
|---|---|
| Prolactin | 3.69E−13 |
| MIF | 3.61E−06 |
| OPN | 0.00001 |
| IGF-II | 0.00009 |
| E-Selectin | 0.00155 |
| Leptin | 0.00249 |
| EGF | 0.00382 |
| IL-17 | 0.00313 |
| MPIF.1 | 0.00839 |
| IL.2sRa | 0.49340 |

Figure 3:
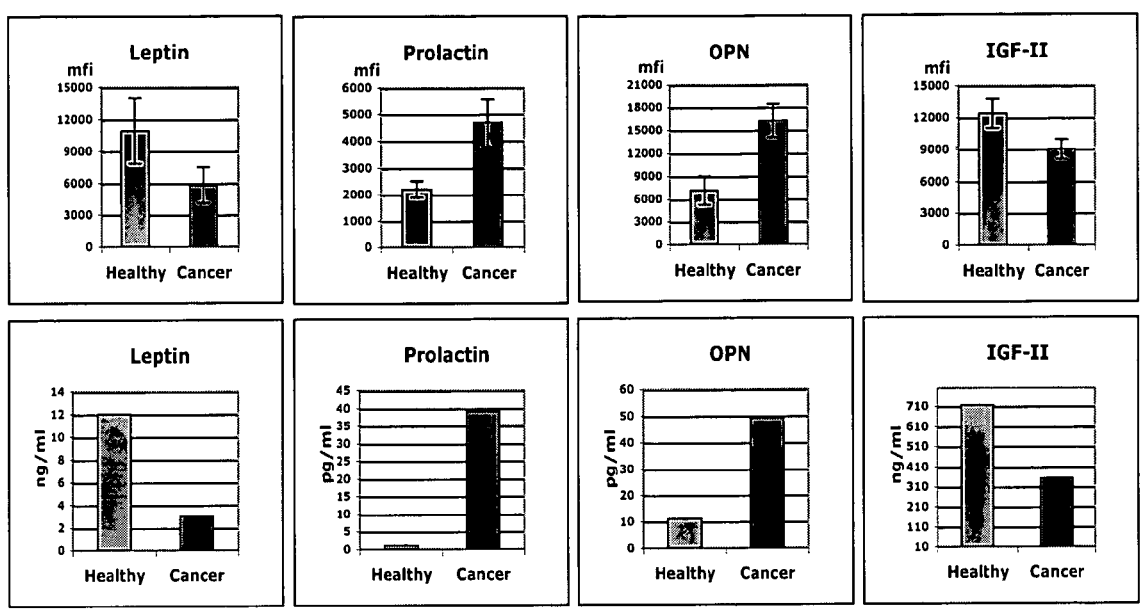
FIG. 3 shows the difference in expression of four proteins (leptin, prolactin, OPN and IGF-II) in subjects with ovarian cancer and in healthy subjects using two different assays: RCA microarray immunoassay and ELISA.

Of these 10 proteins, some of the proteins that showed the most potential for differentiating between not only healthy subjects and subjects newly diagnosed ovarian cancer, but also between healthy subjects and subjects with recurrent disease, were assayed using sandwich Enzyme Linked Immunosorbent Assay (ELISA) on a small cohort of 50 subjects (25 cancer subjects with Stage III/IV ovarian cancer and having an average age of 63.4 years and 25 healthy subjects having an average age of 57 years). Based on ELISA testing of the original sample set, EGF, TNFa, and IL-17 did not provide consistent differentiation between the cancer and control serum samples. MIF-1 was a promising marker but ELISA kits were not reliably available to continue testing. As shown in FIG. 3, four proteins showed perfect correlation between the RCA microarray immunoassays and the ELISA assays. The average concentrations of the four biomarkers determined for these samples are shown below in Table 4.

TABLE 4

Average protein levels for each of the four biomarkers (specific for the ELISA tests used).
Comparison of Average Protein Levels in Sera of Healthy vs. Ovarian Cancer Patients

|  | Leptin (ng/ml) | Prolactin (ng/ml) | OPN (ng/ml) | IGF-II (ng/ml) |
|---|---|---|---|---|
| Normal Range | [7-50] | [0-25] | [0-19] | [450-2500] |
| Healthy | 12 | 1 | 11 | 716 |
| Ovarian Cancer | 3 | 40 | 49 | 350 |

As determined experimentally above using a specific ELISA test, the predetermined standard of leptin is 7-50 ng/ml; the predetermined standard of prolactin is 0-10 pg/ml; the predetermined standard of OPN is 0.5-19 pg/ml; and the predetermined standard of IGF-II is 450-2500 ng/ml. A person of skill in the art would understand that the predetermined standard concentration of a biomarker may vary from assay to assay depending on various factors.

A final panel of four biomarkers (leptin, prolactin, OPN and IGF-II) were selected for assay in a blind study consisting of 206 serum samples which included samples from 106 healthy subjects and 100 ovarian cancer subjects Stages I-IV. The characteristics of the subjects used in this blind study are described in Table 5. The expression of these four biomarkers was determined by ELISA.

TABLE 5

Disease Status and Ages Of Patient Population Participating in Blind Study

|  | Masked Group (n = 206) | Average Age |
|---|---|---|
| Healthy Women |  |  |
| Healthy | 66 | 58.4 |
| High-risk | 40 | 57.6 |
| Women with Ovarian Cancer |  |  |
| Stage I/II | 24 | 59.5 |
| Stage III/IV | 76 | 63 |

Figure 4:
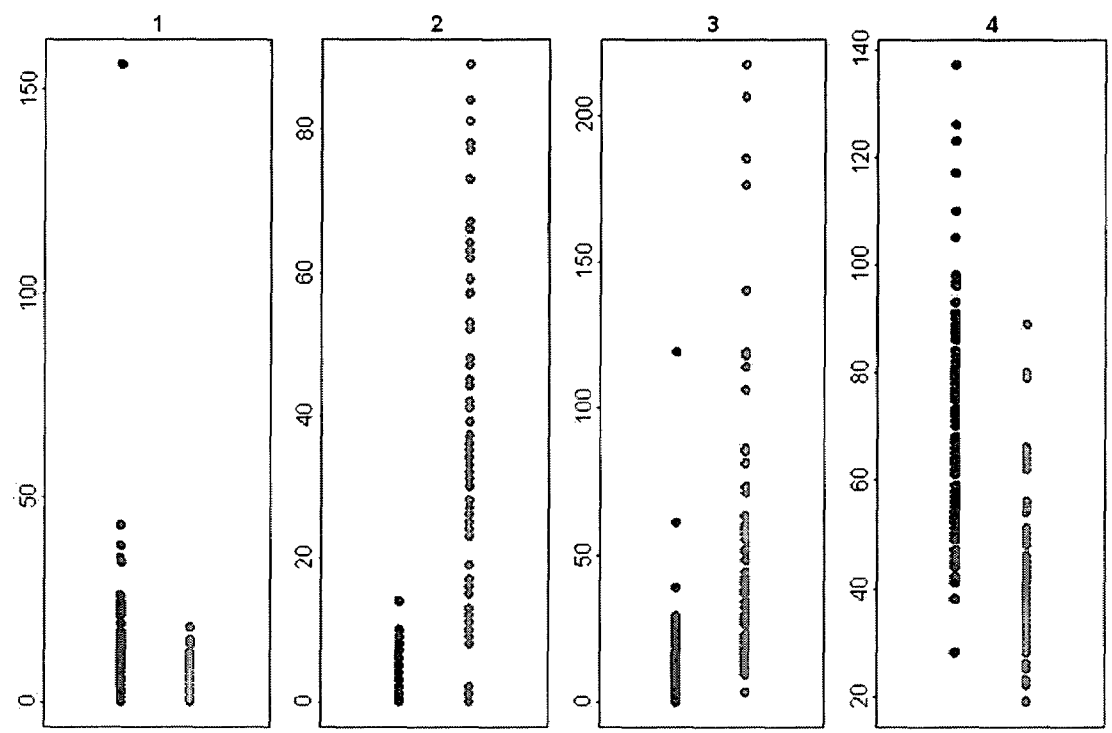
FIG. 4 shows results of analysis of the expression data of four proteins (leptin (identified as "1"), prolactin (identified as "2"), OPN (identified as "3") and IGF-II (identified as "4")) in 206 subjects, using the least square fit in a traditional binary data set analysis. The protein levels of healthy subjects are shown in black (left) and those for subjects with ovarian cancer are shown in gray (right)
Figure 5:
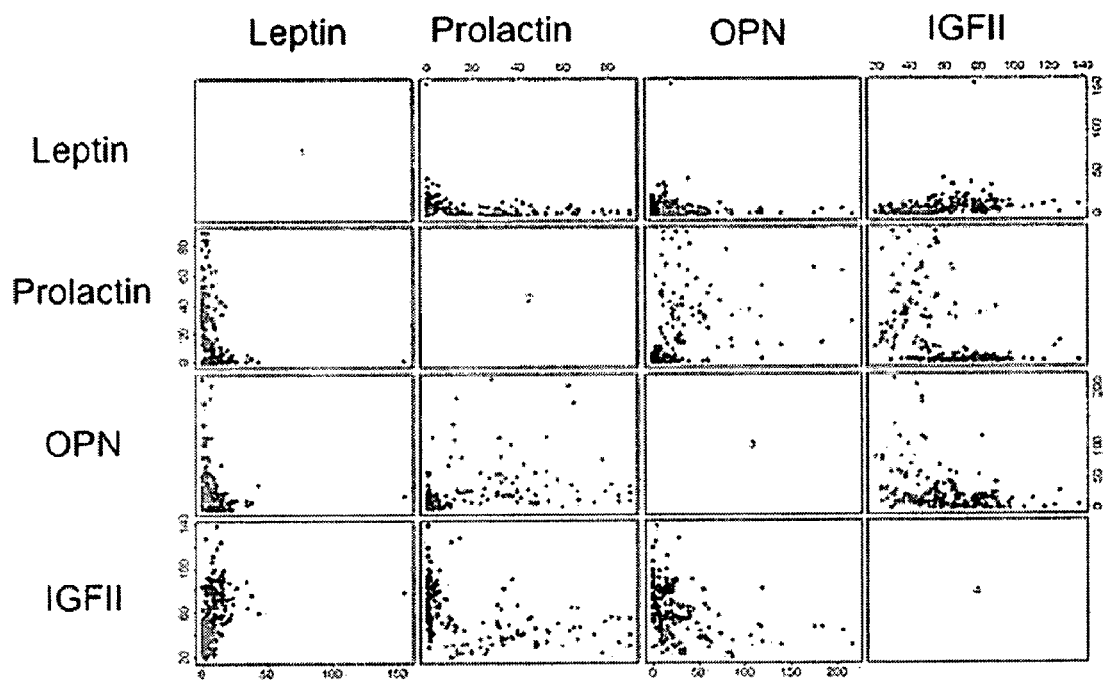
FIG. 5 shows results of analysis of the expression data of four proteins (leptin (identified as "1"), prolactin (identified as "2"), OPN (identified as "3") and IGF-II (identified as "4")) in 206 subjects, using pair plots. The data points derived from healthy subjects are in black and the data points derived from subjects with ovarian cancer are in gray.

To differentiate between subjects with ovarian cancer and healthy subjects, statistical cluster analysis was performed. Although none of the four markers could reliably separate the normal and cancer groups using the least squares fit in a traditional binary data set analysis (FIG. 4), pair plots of the four markers showed better separation between subjects these groups (FIG. 5).

The combined data for the four biomarkers was analyzed by four different classifiers: support vector machines (SVM), k-nearest neighbor classifiers (k-NN), classification trees, and a score-based classification system to classify samples from healthy subjects and samples from subjects with ovarian cancer. Support vector machines (SVM), k-nearest neighbor classifiers (k-NN), classification trees are hierarchical clustering models.

Figure 6:
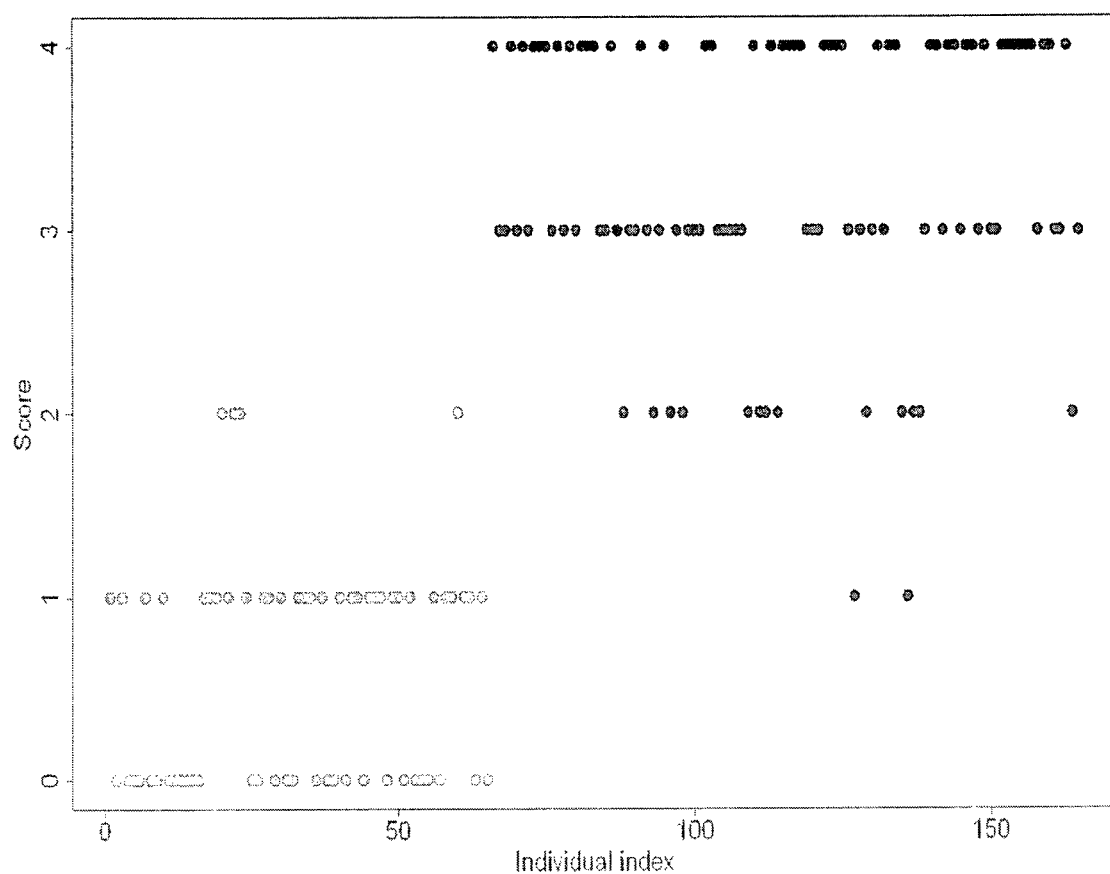
FIG. 6 shows the scores assigned to 206 subjects including 106 healthy subjects and 100 subjects with ovarian cancer based on the score-based classification system described herein. Subjects having a score greater than or equal to 2 can be diagnosed with ovarian cancer, while subjects with score less than or equal to 1 can be diagnosed as free of ovarian cancer. The data points derived from healthy subjects are in light gray and the data points derived from subjects with ovarian cancer are in dark gray.

FIG. 6 shows the result of the score based classification system. Particularly, FIG. 6 shows the scores assigned to the 206 subjects who participated in the phase of the screening assay. The scores were assigned using the following method: For each marker, the best split point to minimize the number of misclassified subjects was found. The split point divides the sample space into two intervals: one for healthy and another for cancer. A score 0 is assigned to a subject if its related observation falls in the normal interval; otherwise, a score 1 is assigned. Table 6 shows the split point for each of the four biomarkers described above. Overall, an individual is assigned a score as the sum of these assigned scores from 4 different markers. Thus, in this instance the range of such score is [0, 4]. FIG. 6 illustrates that subjects having a score greater than or equal to 2 are likely to have cancer; and subjects with a score less than or equal to 1 are likely to be healthy.

TABLE 6

Scoring Criteria for Biomarkers

| Biomarker | Split point | Left interval | Right interval |
|---|---|---|---|
| Leptin (1) | 2.5 ng/ml | Cancer (1) | Normal (0) |
| Prolactin (2) | 10 pg/ml | Normal (0) | Cancer (1) |
| OPN (3) | 21 pg/ml | Normal (0) | Cancer (1) |
| IGF-II (4) | 491 ng/ml | Cancer (1) | Normal (0) |

Table 7 gives classification results based on 10-fold cross-validation for all four classification methods considered. The results indicated that all the classification methods can well distinguish normal and cancer groups. The proposed score based classification method performed better than the nearest neighbor and classification tree methods. The results from the scoring method are comparable to those of SVM. The sensitivity of the test is 96%, specificity 97%, PPV 97% and NPV 96%. The "sensitivity" of an assay refers to the probability that the test will yield a positive result in an individual afflicted with ovarian cancer. The "specificity" of an assay refers to the probability that the test will yield a negative result in an individual not afflicted with ovarian cancer. The "positive predictive value" (PPV) of an assay is the ratio of true positive results (i.e. positive assay results for patients afflicted with ovarian cancer) to all positive results (i.e. positive assay results for patients afflicted with ovarian cancer +positive assay results for patients not afflicted with ovarian cancer).

TABLE 7

Classification results based on 10-fold cross-validation.

| Classification Method | False Positive | False Negative |
|---|---|---|
| SVM | 3/106 | 4/100 |
| TREE | 10/106 | 7/100 |
| k-NN | 6/106 | 10/100 |
| Score-based | 6/106 | 4/100 |

Finally, an additional validation blind study was performed on forty (40) samples using the score-based classification system discussed above. This method was able to accurately classify 38 out of the 40 subjects as having ovarian cancer or not (one sample was classified as a false positive and another sample was classified as a false negative).

Table 8 summarizes the level of four biomarkers identified herein (leptin, prolactin, ODN and IGF-II) and biomarker CA125 in subjects having stage I and stage II ovarian cancer who participated in the screening assays described above (phase IV and V), as determined by the ELISA assays described herein. (The patients in bold/italics participated in phase V of the screening assay described herein).

TABLE 8

Expression levels of biomarkers in patients with Stage I and Stage II ovarian cancer.

| Patient Code | Sample Description | Leptin | Prolactan | OPN | IGF-II | CA125 |
|---|---|---|---|---|---|---|
| | Stage 1 | | | | | |
| C4 | Stage IC Rec granulosa cell OVCA | 11 | 45 | 10 | 547 | 14 |
| C69 | Stage I OVCA (Cellular fibroma) | 0.2 | 35 | 23 | 484 | ND |
| C113 | Stage IA OVCA/endo CA | 9 | 70 | 32 | 475 | 6 |
| C114 | Stage IA | 2 | 24 | 22 | 319 | ND |
| *C155* | *Stage IA OVCA* | *0* | *39* | *39* | *555* | *53.8* |
| *C169* | *Stage IA OVCA* | *1* | *1* | *38* | *821* | *15* |
| | Stage II | | | | | |
| C6 | Stage II Bilateral dysgerminoma (germ-cell OVCA) | 11 | 63 | 38 | 638 | 51.2 |
| C8 | Stage II A/II C OVCA | 3 | 30 | 28 | 513 | 57.3 |
| C9 | Stage II C clear cell OVCA | 3 | 81 | 40 | 553 | 981 |
| C16 | Stage II C malig steroid cell OVCA | 1 | 36 | 106 | 381 | 15 |
| C19 | Stage II C Papillary serous OVCA | 2 | 10 | 86 | 193 | |
| C24 | Stage II C Papillary serous OVCA | 0 | 37 | 21 | 364 | 122 |
| C328 | Stage II C Papillary serous OVCA | 1 | 48 | 10 | 302 | 977 |
| C48 | Stage II Bilateral dysgerminoma(germ-cell OVCA) | 10 | 37 | 42 | 894 | 125 |
| C59 | Stage II A/II C OVCA | 1 | 12 | 16 | 421 | 57.3 |
| C62 | Stage II C OVCA | 0.2 | 35 | 23 | 484 | ND |
| C63 | Stage II C OVCA | 3 | 81 | 40 | 553 | 981 |
| C70 | Stage II C borderline OVCA | 1 | 84 | 21 | 543 | 119 |
| C71 | Stage II Small cell OVCA | 0 | 28 | 217 | 303 | ND |
| C77 | Stage II B serous cell OVCA | 5 | 77 | 81 | 230 | 99.2 |
| C89 | Stage II A OVCA | 12 | 16 | 13 | 431 | 405 |
| C102 | Stage II C OV Adenocarcinoma | 9 | 1 | 32 | 634 | |
| C103 | Stage II osteogenic sarcoma OVCA | 9 | 27 | 51 | 371 | 46.9 |
| C117 | Stage II B/L Stage II C Papillary serous OVCA | 0 | 119 | 48 | 260 | 634 |
| C120 | Stage II C OVCA | 0 | 57 | 41 | 124 | 99 |
| C135 | Stage II C OVCA | 0 | 78 | 29 | 501 | 173 |
| *C165* | *Stage II OVCA* | *9* | *50* | *27* | *576* | *273* |

Materials and Methods Used in Example 1

Microarray Manufacture: Microarrays were prepared according to Schweitzer et al., *Nat Biotech* (2002) 20:359. In short, glass slides were cleaned and derivatized with 3-cyanopropyltriethoxysilane. The slides were equipped with a Teflon mask, which divided the slide into sixteen 0.65 cm diameter wells or circular analysis sites called subarrays (FIG. 2). Printing was performed with a Perkin-Elmer SpotArray Enterprise non-contact arrayer equipped with piezoelectric tips, which dispense a droplet (~350 pL) for each microarray spot. Antibodies were applied at a concentration of 0.5 mg/mL at defined positions. Each chip was printed with sixteen copies of one type of array, either array 1, 2, 3, 4, 5 or 6. (See Table 1.) A set of antibodies was printed with quadruplicate spots in each subarray. After printing, chips were inspected using light microscopy. If the percentage of missing spots observed was greater than 5%, then the batch failed and the slides were discarded immediately. For all print runs described herein, 100% of the antibody features and >95% of the biotin calibrators were printed. Microarray chips were validated in concert with a set of qualified reagents in two ways. First, mixtures of 1-3 different cytokines were prepared so as to provide a high intensity signal and applied to 14 wells on a chip (each well treated with a different mixture up to the total complement of detector antibodies) and two arrays were used as blank controls. The chips were developed and scanned and the resulting signals were compared to the positional map of the particular array. Second, a titration QC for all analytes of a specified array using known sample matrices was performed. Normal human serum and heparinized plasma were assayed neat or spiked with purified recombinant cytokines representing all analytes in the array. Spiked mixtures were then titrated down the subarrays of a slide from 9,000 pg/mL to 37 pg/mL of spiked cytokine concentrations along with two subarrays for each un-spiked control sample. The data was quantified and for every analyte in the array a titration curve was generated to examine feature intensity behavior as a function of concentration. Taken together, this data was used to confirm the activity of array features and reagent sets.

RCA Microarrray Immunoassay: Prior to assay, the slides were removed from storage at room temperature in sealed containers and opened in a humidity controlled chamber (45-55%). Slides were blocked with Seablock (Pierce Chemical Co.), diluted 1:1 with PBS for 1 h at 37° C. in a humidified chamber. Following removal of the blocking solution, they were washed twice with 1×PBS/0.5% Brij 35 prior to application of sample. Four controls were included on each sample slide with feature concentrations corresponding to four anchor points on the full titration curve. The test samples were assayed on the remaining 12 subarrays. Twenty μL of the treated sample were then applied to each subarray. The basics of performing immunoassays with RCA signal amplification has been described (Schweitzer et al., Nat. Biotechnol. (2002) 20:359-65) and we are using SOPs derived from the protocols used in that study. Slides were scanned using a LS200 scanner (TECAN). Scanned images were analyzed using proprietary software. The fluorescence intensity of microarray spots was analyzed for each feature and sample, and the resulting mean intensity values were determined. Dose-response curves for selected cytokines were examined, ensuring that feature intensity is above background and exhibiting increasing intensity with increasing analyte concentration.

Subject Population for RCA microarray immunoassay: For the RCA microarray immunoassays the serum from 86 subjects was assayed. Of the 86 subjects, 28 were healthy and had an average age of 60.8 years, 58 had Stage III/IV ovarian cancer and had an average age of 57.1. Of the 58 patients with Stage III/IV ovarian cancer, 18 were newly diagnosed and the remaining 40 were subjects with recurrent disease.

Subject Population for Blind Study (ELISA): For the panel of ELISA, serum samples were collected from 100 subjects with ovarian cancer and 106 healthy/disease-free or high-risk subjects (as part of the Yale New Haven Hospital Early Detection program (HIC10425). The normal group consisted of 66 healthy/disease-free (including the 28 healthy samples sent for the arrays) and 40 women considered to be at high-risk. Of the 100 ovarian cancer patients, 24 women were diagnosed with Stage I/II and 76 women with Stage III/IV EOC. Included in this group were the 18 newly diagnosed OVCA samples. Serum from the healthy/disease-free group served as baseline values or "normal range" values for the presence of carcinoma.

Sera Collection: 10 ml of blood was collected, centrifuged at 1500 rpm for 10 min. and the serum stored at −80° C. in the OB/GYN Tissue bank until further use. Collection, preparation and storage of the blood samples were done utilizing guidelines set by the NCI Intergroup Specimen Banking Committee. Consent for participation in this study was obtained by qualified personnel. Before analyses, the sera was thawed once and 8 (25-50 ul) aliquots stored at −80° C. to ensure unnecessary freezing and thawing.

ELISA Assay: The leptin, prolactin and IGF-II kits were purchased from Diagnostic Systems Laboratories, Inc. Webster, Tex. and the OPN (Osteopontin) from Assay Designs, Inc. (Ann Arbor, Mich.). Assays were performed following kit instructions, and the results were read on a Spectra Max M2 Microplate Reader (Molecular Devices, Sunnyvale Calif.) set to a dual wavelength of 405 nM with the appropriate correction for each assay. Three classifiers: support vector machines (SVM), K-nearest neighbor classifiers (k-NN) and classification trees were used to analyze results (distinguish the healthy/disease/free from the ovarian cancer patients).

Statistical Analysis: Analysis of variance (ANOVA) was used to test the significance of the protein expression differences detected by RCA microarray immunoassays between subjects with ovarian cancer and healthy subjects, using the GLM procedure of SAS. Reported effect size measures the difference in mean between two groups, normalized by within group standard deviation, and is independent of the sample size:

$$\text{Effect Size} = (\text{Mean\_Group1} - \text{Mean\_Group2}) / \text{Std\_Group1\_Group2}$$

Effect size has a direct association with the predictive ability of a particular variable. Table 9 shows conversions of effect sizes (column 1) to probability (column 2). The example presented in Table 9 is intended to demonstrate the relationship between effect size and predictive ability. For example, with an effect size of 0.3 observed between the two groups, the probability of correctly identifying the groups is 0.56. With an effect size of 1, the probability increases to 0.69.

TABLE 9

Effect size as the measure of predictive ability.

| Effect Size | Probability that grouping could be correctly assigned based on protein expression |
|---|---|
| 0 | 0.5 |
| 0.1 | 0.52 |
| 0.2 | 0.54 |
| 0.3 | 0.56 |
| 0.4 | 0.58 |
| 0.5 | 0.6 |
| 0.6 | 0.62 |
| 0.7 | 0.64 |
| 0.8 | 0.66 |
| 0.9 | 0.67 |
| 1 | 0.69 |
| 1.2 | 0.73 |
| 1.4 | 0.76 |
| 1.6 | 0.79 |
| 1.8 | 0.82 |
| 2 | 0.84 |
| 2.5 | 0.89 |
| 3 | 0.93 |

To differentiate between normal/high risk and ovarian cancer patients, statistical cluster analysis was performed on 4 protein expression markers obtained from patient serum. Three commonly used classification methods were used: support vector machine (SVM), k-nearest neighbors (kNN), and classification trees (Hastie, et al. 2001). We used 10-fold cross validation to evaluate the classification accuracy.

In addition to these three classification methods, we used a score-based classification method that is more biologically interpretable. The score-based classification system can be carried out as follows: (i) For each marker, find the best split point to minimize the number of misclassified subjects. The split point defines two intervals: one for normal and another for cancer. A score of 0 is assigned to a subject if its related observation falls in the normal interval; otherwise, a score of 1 is assigned. (ii) Overall, a subject is assigned a score as the sum of these assigned scores from m different markers. Therefore, the range of such score is between 0 and m. (iii) A given threshold (t) is used to predict the disease status for a given subject, e.g. a given subject with a total score equal or less than t is predicted to have normal status, whereas a subject with a score higher than t will be diagnosed to have disease.

The "split point" described above in connection to the described score based classification system may be identified as follows: Suppose there are n samples classified into two groups. For each marker X, let $x\_1, x\_2, \ldots, x\_n$ be the observed measurements. We screen (n−1) split points $y\_1, y\_2, \ldots, y\_(n-1)$, where $y\_k = 0.5*(x\_k + x\_(k+1))$ for $k=1, 2, \ldots, n-1$. For each split point $y\_k$, there are $a\_1$ and $a\_2$ observed measurements less than $y\_k$ in the first and the second groups, respectively; and there are $b\_1$ and $b\_2$ observed measurements greater than $y\_k$ in the first and the second groups, respectively. If the left and the right sides of $y\_k$ are assigned to the first and the second groups, respectively, then there are a_2 and b_1 misclassified samples. If the left and the right sides of y_k are assigned to the second and the first groups, respectively, then there are a_1 and b_2 misclassified samples. We choose the assignment that minimizes the number of misclassified samples.

Discussion

Ovarian cancer is a "relatively silent" disease with intra-abdominal inaccessibility which makes the monitoring and early detection of the disease utilizing a non-invasive approach such as serum tumor markers an attractive idea. A simple, reliable, reproducible and rapid screening strategy with adequate sensitivity for early detection is needed to improve our ability to accurately detect pre-malignant change or early stage ovarian cancer in asymptomatic women at increased risk for the development of ovarian cancer. It has been suggested that, in order to be acceptable, any screening strategy for early detection must achieve a minimum of 99.6% specificity, hence the need for a combined regimen of tests since it is unlikely that any single analyte test will be that specific. In fact, given the rarity of ovarian cancer, very low levels of false positive classification will result in a large number of women being incorrectly classified as potentially ovarian cancer patients if biomarker screening tests are used as the only means of classification. We assert that initial serum screening for a combination of analytes, followed by transvaginal ultrasound and mammography or thermal breast imaging, should provide a sufficiently low false positive rate to justify subsequent laparoscopic surgery on individuals with detectable pelvic masses to validate the results of the diagnostic assay. This approach is supported by results of studies in which the combination of CA125 and transvaginal ultrasound detected a significant proportion of preclinical ovarian cancers (Jacobs, Mol Cell Proteomics 3(4):355-366 (2004).

Our approach to identify serum biomarkers was based on a strategy of screening multiple serum proteins by high-throughput microarray analysis to identify biomarkers that had the potential to accurately discriminate between healthy/high-risk and cancer and still have the sensitivity to detect early stage I and II ovarian cancers. Based on the microarray results, a promising subset of biomarkers were selected for further analysis by ELISA. Four of the biomarkers selected based on the microarray data were confirmed as useful for early detection and a high level of sensitivity/specificity using ELISA analysis. Initial confirmation of the utility of biomarkers does not require many analyses if high specificity and sensitivity is sought. Biomarkers can be eliminated based on analysis of 15-20 normal and patient samples once quality control of the ELISA in the hands of the technician performing the assay is established. Analysis of a larger number of samples is required for application of statistical techniques (such as SVM, k-NN and Tree), to determine sensitivity/specificity, split-points and combinatorial strategies. After validating the contribution that each biomarker may contribute to a combined assay, split points for each biomarker are defined and the utility of combinations of two or more markers are explored statistically. Using split points the status of each biomarker is assigned as a binary result (normal versus abnormal levels). The number of biomarkers classified as abnormal is used to define an individual as having or not having cancer; in this case, individuals with three or four biomarkers that are abnormal are classified as having ovarian cancer while subjects with two or fewer biomarkers that are abnormal are classified as not having cancer. The biomarkers as individual analytes may not have sufficient sensitivity and specificity, rather the combination of biomarkers may be required for a diagnostic test.

Example 2

The Used of the Biomarkers Identified in Ovarian Cancer Patients to Diagnose Breast Cancer and Colon Cancer Certain samples were analyzed to determined whether the biomarkers identified above (leptin, prolactin, OPN and IGF-II) were differentially expressed in other types of cancer. The results, shown in Table 9, indicate that the biomarkers identified above can be used to diagnose other types of cancer including breast cancer and colon cancer.

As shown in Table 10, samples corresponding to subjects with cancer could be distinguished from samples from healthy subjects by the differential expression of two or more biomarkers as compared to their predetermined standard. In Table 10, the expression levels indicated in italics and bold corresponds to expression levels outside of the predetermined standard for said biomarker.

TABLE 10

Analysis of the expression of leptin, prolactin, OPN and IGF-II in breast cancer and colon cancer.

| Patient Code | Sample Description | Leptin (ng/ml) | Prolactin (pg/ml) | OPN (pg/ml) | IGF-II (ng/ml) | CA125 |
|---|---|---|---|---|---|---|
| | Breast Cancer | | | | | |
| C51 | Stage I Breast Cancer Feb. 8, 2000 @ Age 42 | *3* | *15* | *26* | 540 | ND |
| C57 | Fibrocystic breast mass (No Breast Cancer) | 3 | 0 | *31* | 770 | 8.3 |
| C66 | Mesothelial cysts/Breast Cancer (ductal) 2001/Tamox | *0* | 78 | 23 | 460 | ND |
| C92 | Stage I Breast Cancer Feb. 8, 2000 @ Age 42 | *5* | 1 | *38* | 780 | ND |
| C29 | Stage IV Breast Cancer | *1* | *19* | 30 | *250* | ND |

TABLE 10-continued

Analysis of the expression of leptin, prolactin, OPN and IGF-II in breast cancer and colon cancer.

| Patient Code | Sample Description | Leptin (ng/ml) | Prolactin (pg/ml) | OPN (pg/ml) | IGF-II (ng/ml) | CA125 |
|---|---|---|---|---|---|---|
| | Colon Cancer | | | | | |
| C107 | Stage 1V Colon Cancer/OVCA | 0 | 16 | 216 | 440 | ND |
| C52 | Stage 111 Colon Cancer/OV Cysts | 6 | 51 | 36 | 592 | ND |

INCORPORATION BY REFERENCE

All of the publications cited herein are hereby incorporated by reference in their entirety to describe more fully the art to which the application pertains.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed as new and desired to be protected by Letters Patent of the United States is:

1. A method for diagnosing or aiding in the diagnosis of ovarian cancer in a subject comprising;
   (a) measuring the expression levels of four or more biomarkers in a sample from a subject, wherein four of the biomarkers are prolactin, osteopontin (OPN), leptin, and insulin-like growth factor II (IGF-II);
   (b) comparing the expression level of prolactin, OPN, leptin, and IGF-II to a predetermined standard for prolactin, OPN, leptin, and IGF-II, respectively, wherein a significant difference in the expression level of two or more of the prolactin, OPN, leptin, and IGF-II biomarkers in the sample as compared to a predetermined standard for each of the prolactin, OPN, leptin, and IGF-II biomarkers diagnoses or aids in the diagnosis of ovarian cancer, and wherein a significant difference in the expression level for prolactin or OPN is an increase in the expression level of prolactin or OPN compared to the predetermined standards for prolactin and OPN, respectively; and a significant difference in the expression level for leptin or IGF-II is a decrease in the level of expression of leptin or IGF-II compared to the predetermined standards for leptin and IGF-II, respectively.

2. The method of claim 1, wherein the predetermined standard corresponds to: (a) the expression levels of the biomarker in healthy subjects, or (b) the expression levels of the biomarker in non-cancerous tissue from the same subject.

3. The method of claim 1, wherein each biomarker is assigned a score of 0 or 1, wherein a biomarker is assigned a score of 0 if the expression of the biomarker is not significantly different from the expression of the biomarker in a predetermined standard and wherein a biomarker is assigned a score of 1 if the expression of the biomarker is significantly different from the expression of the biomarker in a predetermined standard; wherein the subject is assigned an overall score which corresponds to the sum of the assigned scores from four or more different markers; and wherein a given threshold (t) is used to diagnose or aid in the diagnosis of cancer.

4. The method of claim 1, further comprising measuring expression of cancer antigen 125 (CA 125) as a biomarker for ovarian cancer.

5. The method of claim 4, wherein a biomarker for ovarian cancer in addition to prolactin, OPN, leptin, and IGF-II is selected from the group: MIF, E-selectin, EGF, IL-17, MPIF, 1, and IL-2sRa.

6. The method of claim 1, wherein a biomarker for ovarian cancer in addition to prolactin, OPN, leptin, and IGF-II is selected from the group: 6Ckine, angiotensin converting enzyme (ACE), brain-derived neurotrophic factor (BDNF), E-Selectin, epidermal growth factor (EGF), eotaxin-2 (Eot-2), epidermal growth factor receptor 1 (ErbB 1), follistatin, hemofiltrate CC chemokine 4 (HCC4), herpes virus entry mediator (HVEM), insulin-like growth factor binding protein 2 (IGFBP-1), interleukin-17 (IL-17), interleukin 1 soluble receptor II (IL-1sRII), interleukin 2 soluble receptor alpha (IL-2 sRα), macrophage colony stimulating factor receptor (M-CSF R), macrophage migration inhibitory factor (MIF), macrophage inflammatory protein 1 alpha (MIP-1α), macrophage inflammatory protein 3 beta (MIP3β), matrix Metalloproteinase-8 (MMP-8), matrix metalloproteinase 7 (MMP-7), myeloid progenitor inhibitory factor 1 (MPIF-1), pulmonary and activation-regulated chemokine (PARC), platelet-derived growth factor receptor beta (PDGF Rβ), protein C, tumor necrosis factor receptor 1 (TNF-RI), tumor necrosis factor alpha (TNF-α), soluble Vascular Adhesion Protein-1(sVAP-1), vascular endothelial growth factor receptor 2 (VEGF R2), VEGF receptor 3 (VEGF R3), human stratum corneum chymotryptic enzyme (HSCCE), kallikrein 4, kallikrein 5, kallikrein 6 (protease M), kallikrein 8, kallikrein 9, kallikrein 10, cancer antigen 125 (CA 125), CA15-3, CA19-9, OVX1, lysophosphatidic acid (LPA), carcinoembryonic antigen (CEA), macrophage colony-stimulating factor (M-CSF), prostasin, CA54-61, CA72, HMFG2, interleukin-6 (IL-6), interleukin-10 (IL-10), LSA, NB70K, PLAP, TAG72, TPA, UGTF, WAP four-disulfide core domain 2 (HE4), matrix metalloprotease 2, tetranectin, inhibin, mesothelyn, MUC1, vascular endothelial growth factor (VEGF) NOTCH3, E2F transcription factor 3 (E2F3), GTPase activating protein (RACGAP1), hemotological and neurological expressed 1 (HN1), apolipoprotein A1, laminin, claudin 3 (CLDN3), claudin 4, tumor-associated calcium signal transducer 1 (TROP-1/Ep-CAM), tumor-associated calcium signal transducer 2 (TROP-2), ladinin 1, S100A2, SERPIN2 (PAI-2), CD24, lipocalin 2, matriptase (TADG-15), stratifin, transforming growth factor-beta receptor III (TGF-β-RIII), platelet-derived growth factor receptor alpha, SEMACAP3, ras homology gene family member I (ARHI), thrombospondin 2, disabled-2/differentially expressed in ovarian carcinoma 2 (Dab2/DOC2), and haptoglobin-alpha subunit.

7. The method of claim 1, wherein a biomarker for ovarian cancer in addition to prolactin, OPN, leptin and IGF-II is selected from the group: MIF, E-selectin, EGF, IL-17, MPIF, 1, and IL-2sRa.

8. The method of claim 1, wherein the sample is a body fluid, cell or tissue sample.

9. The method of claim 8, wherein the body fluid sample is blood or serum.

10. The method of claim 1, further comprising detecting an additional biomarker for ovarian cancer.

11. A method of monitoring the progression of ovarian cancer in a subject comprising
(a) measuring the expression levels of four or more biomarkers in a first sample from the subject and a subsequent sample from the subject, wherein four of the biomarkers are prolactin, osteopontin (OPN), leptin, and insulin-like growth factor II (IGF-II);
(b) comparing the expression of the prolactin, OPN, Leptin, and IGF-II biomarkers in the first sample to the expression of the prolactin, OPN, leptin, and IGF-II biomarkers in the subsequent sample where a significant difference in the expression level of two or more of the prolactin, OPN, leptin, and IGF-II biomarkers in a sample as compared to a predetermined standard for each of the prolactin, OPN, leptin, and IGF-II biomarkers, and a significant difference for prolactin or OPN is an increase in the level of prolactin or OPN compared to the predetermined standards for prolactin and OPN, respectively; and a significant difference for leptin or IGF-II is a decrease in the level of leptin or IGF-II compared to the predetermined standards for leptin and IGF-II, respectively, and wherein an increase in the number of significantly different expression levels of the prolactin, OPN, letin, and IGF-II biomarkers in the first sample compared to the subsequent sample indicates progression of ovarian cancer in the subject and a decrease in the number of significantly different expression levels of the prolactin, OPN, leptin, and IGF-II biomarkers in the first sample compared to the subsequent sample indicates regression of ovarian cancer in the subject.

12. The method of claim 11, further comprising comparing the expression of cancer antigen 125 (CA 125) in the first sample and the subsequent sample.

13. The method of claim 12, wherein a biomarker for ovarian cancer in addition to prolactin, OPN, leptin, and IGF-II is selected from the group: MIF, E-selectin, EGF, IL-17, MPIF,1, and IL-2sRa.

14. The method of claim 11, wherein a biomarker for ovarian cancer in addition to prolactin, OPN, leptin, and IGF-II is selected from the group: MIF, E-selectin, EGF, IL-17, MPIF.1, and IL-2sRa.

15. The method of claim 11, wherein a biomarker for ovarian cancer in addition to prolactin, OPN, leptin, and IGF-II is selected from the group: 6Ckine, angiotensin converting enzyme (ACE), brain-derived neurotrophic factor (BDNF), E-Selectin, epidermal growth factor (EGF), eotaxin-2 (Eot-2), epidermal growth factor receptor 1 (ErbB1), follistatin, hemofiltrate CC chemokine 4 (HCC4), herpes virus entry mediator (HVEM), insulin-like growth factor binding protein 2 (IGFBP-1), interleukin-17 (IL-17), interleukin 1 soluble receptor II (IL-1 sRII), interleukin 2 soluble receptor alpha (IL-2 sRα), macrophage colony stimulating factor receptor (M-CSF R), macrophage migration inhibitory factor (MIF), macrophage inflammatory protein 1 alpha (MIP-1α), macrophage inflammatory protein 3 beta (MIP3β), matrix Metalloproteinase-8 (MMP-8), matrix metalloproteinase 7 (MMP-7), myeloid progenitor inhibitory factor 1 (MPIF-1), pulmonary and activation-regulated chemokine (PARC), platelet-derived growth factor receptor beta (PDGF Rβ), protein C, tumor necrosis factor receptor I (TNF-RI), tumor necrosis factor alpha (TNF-α), soluble Vascular Adhesion Protein-1 (sVAP-1), vascular endothelial growth factor receptor 2 (VEGF R2), VEGF receptor 3 (VEGF R3), human stratum corneum chymotryptic enzyme (HSCCE), kallikrein 4, kallikrein 5, kallikrein 6 (protease M), kallikrein 8, kallikrein 9 kallikrein 10, cancer antigen 125 (CA 125), CA15-3, CA19-9, OVX1, lysophosphatidic acid (LPA), carcinoembryonic antigen (CEA), macrophage colony-stimulating factor (M-CSF), prostasin, CA54-61, CA72, HMFG2, interleukin-6 (IL-6), interleukin-10(IL-10), LSA, NB70K, PLAP, TAG72, TPA, UGTF, WAP four-disulfide core domain 2 (HE4), matrix metalloprotease 2, tetranectin, inhibin, mesothelyn, MUC1, vascular endothelial growth factor (VEGF) NOTCH-3, E2F transcription factor 3 (E2F3), GTPase activating protein (RACGAP 1), hemotological and neurological expressed 1 (HN1), apolipoprotein A1, laminin, claudin 3 (CLDN3), claudin 4, tumor-associated calcium signal transducer 1 (TROP-1/Ep-CAM), tumor-associated calcium signal transducer 2 (TROP-2), ladinin 1, S100A2, SERPIN2 (PAI-2), CD24, lipocalin 2, matriptase (TADG-15), stratifin, transforming growth factor-beta receptor III (TGF-β-RIII), platelet-derived growth factor receptor alpha, SEMACAP3, ras homology gene family member I (ARHI), thrombospondin 2, disabled-2/differentially expressed in ovarian carcinoma 2 (Dab2/DOC2), and haptoglobin-alpha subunit.

16. A method for diagnosing or aiding in the diagnosis of ovarian cancer in a subject comprising;
(a) measuring the expression levels of four or more biomarkers in a sample from a subject, wherein the four biomarkers are prolactin, osteopontin (OPN), leptin, and insulin-like growth factor II (LOP-II);
(b) comparing the expression level of prolactin to a prolactin split point, wherein if the prolactin expression level for the subject is below the prolactin split point, a score corresponding to healthy is assigned and if the prolactin expression level is at or above the prolactin split point, a score corresponding to cancer is assigned;
(c) comparing the expression level of OPN to an OPN split point, wherein if the OPN expression level for the subject is below the OPN split point, a score corresponding to healthy is assigned and if the OPN expression level is at or above the OPN split point a score corresponding to cancer is assigned;
(d) comparing the expression level of leptin to a leptin split point, wherein if the leptin expression level is below the leptin split point a score corresponding to cancer is assigned and if the leptin expression level is at or above the leptin split point a score corresponding to healthy is assigned;
(e) comparing the expression level of IGF-II to an IGF-II split point, wherein if the IGF-II expression level is below the IGF-II split point, a score corresponding to cancer is assigned and if the IGF-II expression level is at or above the IGF-II split point, a score corresponding to healthy is assigned;
(f) calculating the total number of scores corresponding to cancer for the prolactin, OPN, leptin, and IGF-II biomarkers whose expression levels in the sample were determined and comparing the total number of scores corresponding to cancer with a predetermined score (t), wherein a total number of scores corresponding to cancer greater than (t) diagnoses or aids in the diagnosis of ovarian cancer in the subject; and (g) determining the diagnosis or aiding in determining the diagnosis of ovarian cancer in the subject based on the calculation of the total number of scores corresponding to cancer for the prolactin, OPN, Leptin, and IGF-II biomarkers.

17. The method of claim 16, wherein a score corresponding to cancer is 1 and a score corresponding to normal is 0 and wherein a sum of scores for a subject that is two or greater indicates ovarian cancer and a sum of scores for the subject that is less than two indicates healthy.

18. The method of claim 16, further comprising measuring the expression of cancer antigen 125 (CA 125).

19. The method of claim 18, wherein the method further comprises comparing the expression level of CA125 to a predetermined CA125 standard, wherein if the CA125 expression level is above the predetermined CA125 standard, a score corresponding to cancer is assigned and if the CA125 expression level is at or below the predetermined CA125 standard, a score corresponding to healthy is assigned.

20. The method of claim 18, wherein a biomarker for ovarian cancer in addition to prolactin, OPN, leptin, and IGF-II is selected from the group: MIF, E-selectin, EGF, IL-17, MPIF.1, and IL-2sRa.

21. The method of claim 16, wherein a biomarker for ovarian cancer in addition to prolactin, OPN, Leptin, and IGF-II is selected from the group: 6Ckine, angiotensin converting enzyme (ACE), brain-derived neurotrophic factor (BDNF), E-Selectin, epidermal growth factor (EGF), eotaxin-2 (Eot-2), epidermal growth factor receptor 1 (ErbB1), fotlistatin, hemofiltrate CC chemokine 4 (HCC4), herpes virus entry mediator (HVEM), insulin-like growth factor binding protein 2 (IGFBP- 1), interleukin- 17 (IL- 17), interleukin 1 soluble receptor II (IL- 1 sRII), interleukin 2 soluble receptor alpha (IL-2 sRα), macrophage colony stimulating factor receptor (M-CSF R), macrophage migration inhibitory factor (MIF), macrophage inflammatory protein 1 alpha (MIP-1α), macrophage inflammatory protein 3 beta (MIP3β), matrix Metalloproteinase-8 (MMP-8), matrix metalloproteinase 7 (MMP-7), myeloid progenitor inhibitory factor 1 (MPIF-1), pulmonary and activation-regulated chemokine (PARC), platelet-derived growth factor receptor beta (PDGF Rβ), protein C, tumor necrosis factor receptor I (TNF-RI), tumor necrosis factor alpha (TNF-α), soluble Vascular Adhesion Protein-1 (sVAP-1), vascular endothelial growth factor receptor 2 (VEGF R2), VEGE receptor 3 (VEGE R3), human stratum corneum chymotryptic enzyme (HSCCE), kallikrein 4, kallikrein 5, kallikrein 6 (protease M), kallikrein 8, kallikrein 9, kallikrein 10, cancer antigen 125 (CA 125), CA15-3, CA19-9, OVX1, lysophosphatidic acid (LPA), carcinoembryonic antigen (CEA), macrophage colony-stimulating factor (M-CSF), prostasin, CA54-61, CA72, HMFG2, interleukin-6 (IL-6), interleukin-10 (IL-10), LSA, NB70K, PLAP, TAG72, TPA, UGTF, WAP four-disulfide core domain 2 (HE4), matrix metalloprotease 2, tetranectin, inhibin, mesothelyn, MUC1, vascular endothelial growth factor (VEGF), NOTCH3, E2F transcription factor 3 (E2F3), GTPase activating protein (RACGAP1), hemotological and neurological expressed 1 (HN1), apolipoprotein A1, laminin, claudin 3 (CLDN3), claudin 4, tumor-associated calcium signal transducer 1 (TROP-1/Ep-CAM), tumor-associated calcium signal transducer 2 (TROP-2), ladinin 1, S100A2, SERPIN2(PAI-2), CD24, lipocalin 2, matriptase (TADG-15), stratifrn, transforming growth factor-beta receptor III (TGF-β-RIII), platelet-derived growth factor receptor alpha, SEMACAP3, ras homology gene family member I (ARHI), thrombospondin 2, disabled-2/differentially expressed in ovarian carcinoma 2 (Dab2/DOC2), and haptoglobin-alpha subunit.

22. The method of claim 16, wherein the sample is a body fluid, cell, or tissue sample.

23. The method of claim 22, wherein the body fluid sample is blood or serum.

24. The method of claim 16, wherein the prolactin, OPN, leptin, and IGF-II predetermined standards are prolactin, OPN, leptin, and IGF-II split points, respectively, and wherein each split point divides the expression level for its respective biomarker in the sample into two intervals: a first interval for healthy and a second interval for ovarian cancer.

25. The method of claim 16, wherein a biomarker for ovarian cancer in addition to prolactin, OPN, leptin, and IGF-II is selected from the group: MIF, E-selectin, EGF, IL-17, MPIF.1, and IL-2sRa.

26. A method of monitoring the progression of ovarian cancer in a subject comprising:

(a) measuring the expression levels of four or more biomarkers in a first sample from the subject and a subsequent sample from the subject, wherein four of the four or more biomarkers are prolactin, osteopontin (OPN), leptin, and insulin-like growth factor II (IGF-II);

(b) comparing the expression level of prolactin in each sample to a prolactin split point, wherein if the prolactin expression level for a sample is below the prolactin split point, a score corresponding to healthy is assigned to that sample and if the prolactin expression level for a sample is at or above the prolactin split point, a score corresponding to cancer is assigned to that sample;

(c) comparing the expression level of OPN in a sample to an OPN split point, wherein if the OPN expression level for either sample is below the OPN split point, a score corresponding to healthy is assigned to that sample and if the OPN expression level for a sample is at or above the OPN split point, a score corresponding to cancer is assigned to that sample;

(d) comparing the expression level of leptin in a sample to a leptin split point, wherein if the leptin expression level for a sample is below the leptin split point, a score corresponding to cancer is assigned to that sample and if the leptin expression level for a sample is at or above the leptin split point, a score corresponding to healthy is assigned to that sample;

(e) comparing the expression level of IGF-II in each sample to an IGF-II split point, wherein if the IGF-II expression level for a sample is below the IGF-II split point, a score corresponding to cancer is assigned to that sample and if the IGF-II expression level for a sample is at or above the IGF-II split point, a score corresponding to healthy is assigned to that sample;

(f) calculating the total number of scores for each sample corresponding to cancer for the prolactin, OPN, leptin, and IGF-II biomarkers whose expression levels in the samples were determined; and (g) comparing each sample's total number scores corresponding to cancer, wherein a difference in the total number of scores between the first and subsequent samples monitors the progression of the ovarian cancer in the subject.

27. The method of claim 26, wherein the four or more biomarkers comprise prolactin, OPN, leptin, IGF-II and cancer antigen 125 (CA 125).

28. The method of claim 27, wherein a biomarker for ovarian cancer in addition to prolactin, OPN, leptin, and IGF-II is selected from the group: MIF, E-selectin, EGF, IL-17, MPIF.1, and IL-2sRa.

29. The method of claim 26, wherein a biomarker for ovarian cancer in addition to prolactin, OPN, Leptin, and IGF-II is selected from the group: MIF, E-selectin, EGF, IL-17, MPIF, 1 and IL-2sRa.

30. The method of claim 26, wherein a score corresponding to cancer is 1 and a score corresponding to normal is 0 and wherein a sum of scores for the first sample or subsequent sample that is two or greater indicates ovarian cancer for that sample.

31. The method of claim 26, wherein the prolactin, OPN, leptin, and IGF-II predetermined standards are prolactin, OPN, leptin, and IGF-II split points, respectively, and wherein each split point divides the expression level for its respective biomarker in the sample into two intervals: a first interval for healthy and a second interval for ovarian cancer.

32. The method of claim 26, wherein a biomarker for ovarian cancer in addition to prolactin, OPN, leptin, and IGF-II is selected from the group: 6Ckine, angiotensin converting enzyme (ACE), brain-derived neurotrophic factor (BDNF), E-Selectin, epidermal growth factor (EGF), eotaxin-2 (Eot-2), epidermal growth factor receptor 1 (ErbB1), follistatin, hemofiltrate CC chemokine 4 (HCC4), herpes virus entry mediator (HVEM), insulin-like growth factor binding protein 2 (IGFBP-1), interleukin-17 (IL-17), interleukin 1 soluble receptor II (IL-1 sRII), interleukin 2 soluble receptor alpha (IL-2 sRα), macrophage colony stimulating factor receptor (M-CSF R), macrophage migration inhibitory factor (MIF), macrophage inflammatory protein 1 alpha (MIP-1α), macrophage inflammatory protein 3 beta (MIP3β), matrix Metalloproteinase-8 (MMP-8), matrix metalloproteinase 7 (MMP-7), myeloid progenitor inhibitory factor 1 (MPIF-1), pulmonary and activation-regulated chemokine (PARC), platelet-derived growth factor receptor beta (PDGF Rβ), protein C, tumor necrosis factor receptor I (TNF-RI), tumor necrosis factor alpha (TNF-α), soluble Vascular Adhesion Protein-1 (sVAP-1), vascular endothelial growth factor receptor 2 (VEGF R2), VEGF receptor 3 (VEGF R3), human stratum corneum chymotryptic enzyme (HSCCE), kallikrein 4, kallikreiri 5, kallikrein 6 (protease M), kallikrein 8, kallikrein 9, kallikrein 10, cancer antigen 125 (CA 125), CA15-3, CA19-9, OVX1, lysophosphatidic acid (LPA), carcinoembryonic antigen (CEA), macrophage colony-stimulating factor (M-CSF), prostasin, CA54-61, CA72, HMFG2, interleukin-6 (IL-6), interleukin-10 (IL-10), LSA, NB70K, PLAP, TAG72, TPA, UGTF, WAP four-disulfide core domain 2 (HE4), matrix metalloprotease 2, tetranectin, inhibin, mesothelyn, MUC1, vascular endothelial growth factor (VEGF) NOTCH3, E2F transcription factor 3 (E2F3), GTPase activating protein (RACGAP1), hemotological and neurological expressed 1 (HN1), apolipoprotein A1, laminin, claudin 3 (CLDN3), claudin 4, tumor-associated calcium signal transducer 1 (TROP-1/Ep-CAM), tumor-associated calcium signal transducer 2 (TROP-2), ladinin 1, S100A2, SERPIN2(PAI-2), CD24, lipocalin 2, matriptase (TADG-15), stratifin, transforming growth factor-beta receptor III (TGF-β-RIII), platelet-derived growth factor receptor alpha, SEMACAP3, ras homology gene family member I (ARHI), thrombospondin 2, disabled-2/differentially expressed in ovarian carcinoma 2 (Dab2/DOC2), and haptoglobin-alpha subunit.

* * * * *

UNITED STATES PATENT AND TRADEMARK OFFICE
CERTIFICATE OF CORRECTION

PATENT NO. : 7,666,583 B2  
APPLICATION NO. : 11/037889  
DATED : February 23, 2010  
INVENTOR(S) : Gil G. Mor et al.

It is certified that error appears in the above-identified patent and that said Letters Patent is hereby corrected as shown below:

At column 36, claim 6, line 33, please change "insulin-like growth factor binding protein 2 (IGFBP-1)" to "insulin-like growth factor binding protein 1 (IGFBP-1)".

At column 37, claim 15, line 63, please change "insulin-like growth factor binding protein 2 (IGFBP-1)" to "insulin-like growth factor binding protein 1 (IGFBP-1)".

At column 39, claim 21, line 35, please change "insulin-like growth factor binding protein 2 (IGFBP-1)" to "insulin-like growth factor binding protein 1 (IGFBP-1)".

At column 41, claim 32, line 27, please change "insulin-like growth factor binding protein 2 (IGFBP-1)" to "insulin-like growth factor binding protein 1 (IGFBP-1)".

Signed and Sealed this  
Eighteenth Day of December, 2012

David J. Kappos  
*Director of the United States Patent and Trademark Office*